US011975176B2

(12) United States Patent
Slater et al.

(10) Patent No.: US 11,975,176 B2
(45) Date of Patent: May 7, 2024

(54) DEVICES AND METHODS FOR SYRINGES CONFIGURED TO REDUCE OR ELIMINATE RESIDUAL VOLUME

(71) Applicant: Numedico Technologies (IP) Pty Ltd, Adelaide (AU)

(72) Inventors: Brett Hoe Slater, Mount Colah (AU); Gregory James Roger, Laguna (AU)

(73) Assignee: Numedico Technologies (IP) Pty Ltd, Adelaide (AU)

( * ) Notice: Subject to any disclaimer, the term of this patent is extended or adjusted under 35 U.S.C. 154(b) by 0 days.

(21) Appl. No.: 17/958,181

(22) Filed: Sep. 30, 2022

(65) Prior Publication Data
US 2023/0241317 A1 Aug. 3, 2023

(30) Foreign Application Priority Data
Jan. 31, 2022 (AU) ................ 2022900168

(51) Int. Cl.
*A61M 5/19* (2006.01)
*A61M 5/315* (2006.01)
(Continued)

(52) U.S. Cl.
CPC .......... *A61M 5/19* (2013.01); *A61M 5/31513* (2013.01); *A61M 5/322* (2013.01); *A61M 2005/1787* (2013.01)

(58) Field of Classification Search
CPC .... A61M 2005/323; A61M 2005/3231; A61M 2005/3239; A61M 2005/31516; A61M 2005/1787
See application file for complete search history.

(56) References Cited

U.S. PATENT DOCUMENTS 5,795,337 A * 8/1998 Grimard ............ A61M 5/31511
604/222
10,639,429 B2 * 5/2020 Haindl .............. A61M 5/31515
(Continued)

FOREIGN PATENT DOCUMENTS

WO 2021/185810 A1 9/2021

OTHER PUBLICATIONS

Search Report dated Mar. 7, 2023 for counterpart International Patent Application No. PCT/AU2023/050052.

*Primary Examiner* — Emily L Schmidt
(74) *Attorney, Agent, or Firm* — Morgan, Lewis & Bockius LLP

(57) ABSTRACT

The present disclosure relates to a syringe including a container, for containing a primary fluid, and at least one secondary fluid chamber configured to contain a secondary fluid. The container comprises a proximal end and a distal end and having a distal end opening at the distal end. The syringe further comprises a stopper, movably arranged within the container; and a plunger engageable with the stopper and configured to apply a force to the stopper to move the stopper within the container towards the distal end of the container, to expel primary fluid from the container through the distal end opening. The plunger is further configured to expel secondary fluid from the at least one secondary fluid chamber towards the distal end opening, to expel at least a portion of a residual volume of primary fluid through the distal end opening. A plunger system and assembly for a syringe and methods of expelling fluid from a syringe are also disclosed.

21 Claims, 22 Drawing Sheets

(51) Int. Cl.
*A61M 5/32* (2006.01)
*A61M 5/178* (2006.01)

(56) References Cited

U.S. PATENT DOCUMENTS

| | | |
|---|---|---|
| 2002/0091361 A1 | 7/2002 | Rosoff et al. |
| 2011/0224610 A1 | 9/2011 | Lum et al. |
| 2011/0245768 A1 | 10/2011 | Kiehne |
| 2012/0220950 A1* | 8/2012 | Carlyon ............ A61M 5/31596 604/191 |
| 2014/0254303 A1 | 9/2014 | McArthur et al. |
| 2016/0346481 A1 | 12/2016 | Haindl et al. |
| 2018/0264195 A1* | 9/2018 | Hopkins ................. A61M 5/32 |

* cited by examiner

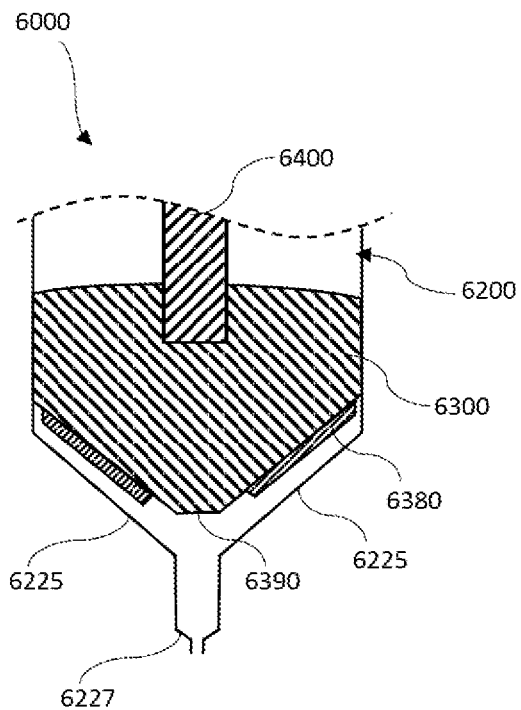 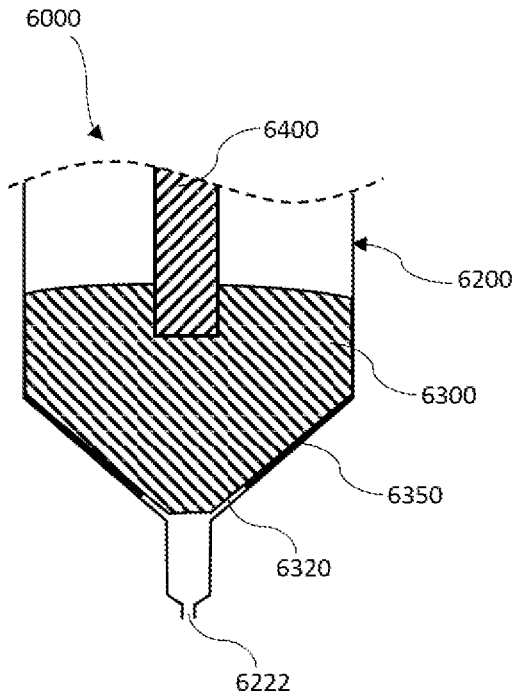
Fig. 6A
Fig. 6B
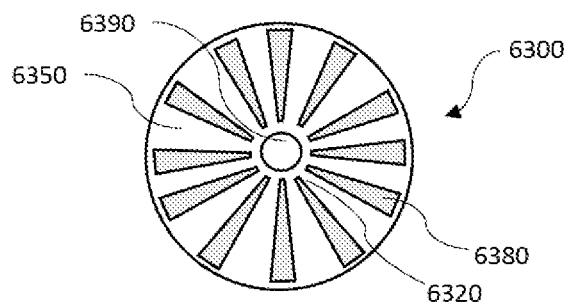
Fig. 6C

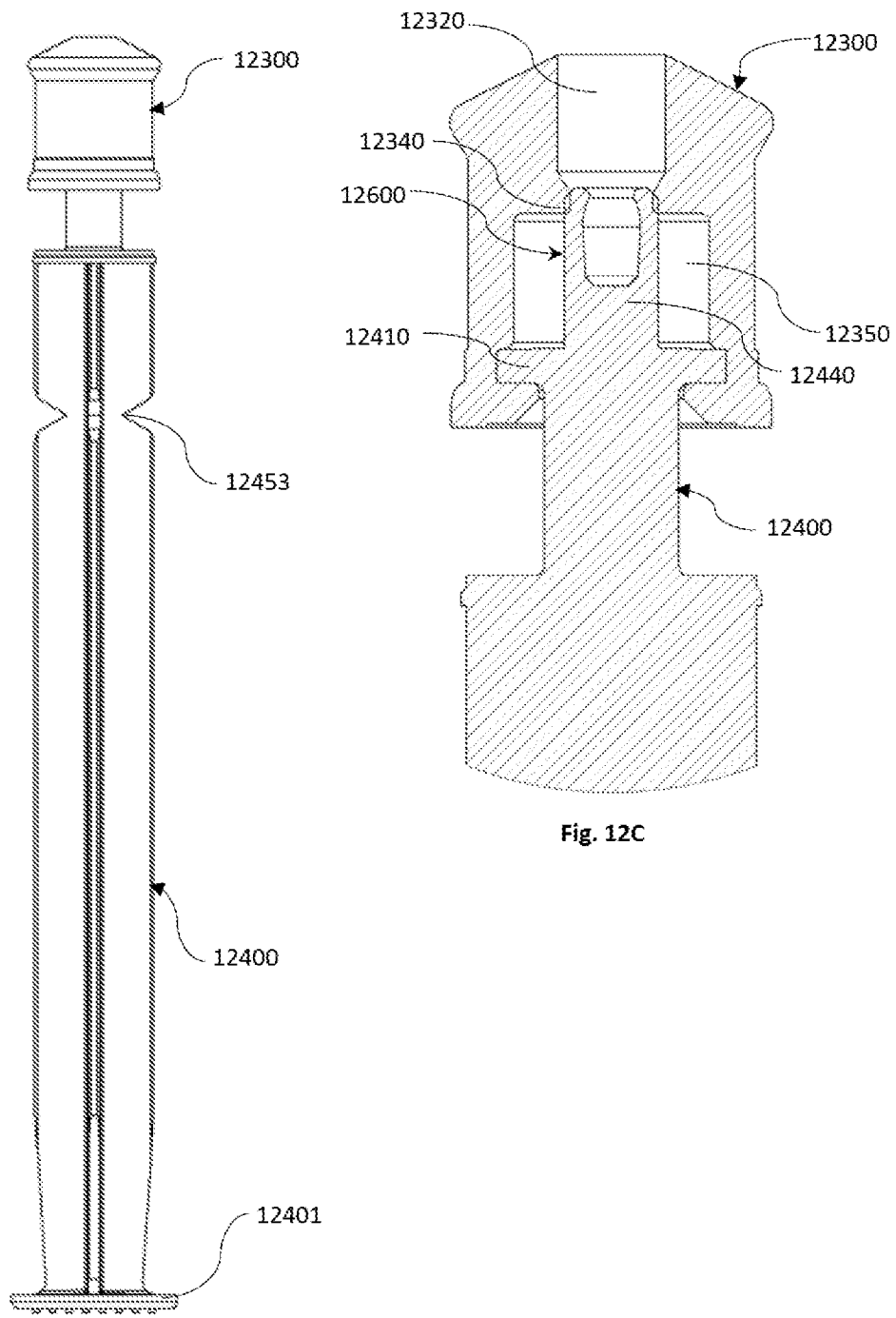

DEVICES AND METHODS FOR SYRINGES CONFIGURED TO REDUCE OR ELIMINATE RESIDUAL VOLUME

CROSS-REFERENCE TO RELATED APPLICATIONS

This application is related to Australian Provisional Application No. 2022900168 entitled, "Devices and Methods for Syringe Configured to Reduce or Eliminate Residual Drug Volume" filed on 31 Jan. 2022. This Australian Provisional Application is incorporated herein by reference in its entirety. In addition, WO 2004/014470 A1 and WO 2018/001624 A1 are each incorporated herein by reference in their entirety.

TECHNICAL FIELD

The present disclosure is related to the field of syringes and more particularly concerns syringes for more complete expulsion of the contents of the syringe.

BACKGROUND

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

Syringes generally comprise an elongate barrel, defining a chamber for receiving a fluid. The syringe barrel generally has a distal end opening allowing expulsion of the fluid and has a syringe tip adapted for mounting a needle thereon. The syringe barrel receives a stopper and plunger assembly, which functions in a piston-like manner such that force applied to the plunger drives the stopper axially along the syringe barrel. The plunger seals against the inner surface of the syringe barrel and may be pulled in a proximal direction to draw up fluid, or pushed in a distal direction to expel fluid from the distal end opening for injection through the cannula of an attached needle.

A residual volume of fluid (residuum) remains in the syringe barrel distal to the plunger and/or in the needle cannula at the end of an injection. For smaller syringes, expensive medications, or medication manufactured in large numbers of doses, this unused medication may represent a significant loss. Further, where medications are scarce or in high demand, the cumulative loss of residuum over many doses may amount to a significant reduction in the number of subjects to which the medication may be delivered.

There is a need in the art for improved delivery devices and methods of use. The present disclosure is directed to overcome and/or ameliorate at least one or more of the disadvantages of the prior art, as will become apparent from the discussion herein. The present disclosure also provides other advantages and/or improvements as discussed herein.

SUMMARY

This summary is not meant to cover each and every embodiment, combination or variations that are contemplated with the present disclosure. Additional embodiments are disclosed in the detailed description, drawings, and claims.

According to at least one embodiment of the present disclosure, there is provided a syringe comprising:
 a container for containing a primary fluid, the container comprising a proximal end and a distal end and having a distal end opening at the distal end;
 a stopper movably arranged within the container; and
 a plunger engageable with the stopper and configured to apply a force to the stopper to move the stopper within the container;
 wherein the syringe comprises at least one secondary fluid chamber configured to contain a secondary fluid;
 wherein the plunger is configured to move the stopper towards the distal end of the container, to expel primary fluid from the container through the distal end opening; and
 wherein the plunger is configured to expel secondary fluid from the at least one secondary fluid chamber towards the distal end opening, to expel at least a portion of a residual volume of primary fluid through the distal end opening.

In general, syringes according to at least one embodiment of the present disclosure may provide a two-stage expulsion of fluid. The first stage may comprise a first ejection of primary fluid from the container, after which a residual volume of primary fluid remains in a portion of the container distal to the plunger and/or in an attached needle cannula. As used herein, "residual volume" refers to a quantity of fluid remaining in the syringe barrel and/or needle cannula after the first action of the syringe. The second stage expulsion may comprise an ejection of secondary fluid from the at least one secondary fluid chamber, thereby to expel at least a portion of the residual volume of primary fluid from the container and the needle cannula.

According to at least one embodiment of the present disclosure, there is provided a method of expelling fluid from a syringe according to one or more of the embodiments disclosed herein, the method comprising:
 engaging the plunger with the stopper;
 applying force to the plunger to at least partially transmit a first force to the stopper to move the stopper within the container towards the distal end of the container, expelling primary fluid from the container through the distal end opening; and
 applying a second force to the plunger to expel secondary fluid from the at least one secondary fluid chamber towards the distal end opening, expelling at least a portion of a residual volume of primary fluid through the distal end opening.

According to at least one embodiment, there is provided a plunger system for a syringe, the plunger system comprising:
 a stopper configured to be movably arranged within a container of the syringe; and
 a plunger engageable with the stopper and configured to apply a force to the stopper to move the stopper within the container,
 wherein the container is configured for containing a primary fluid, the container comprising a proximal end and a distal end and having a distal end opening at the distal end,
 wherein the plunger system comprises at least one secondary fluid chamber configured to contain a secondary fluid;
 wherein the plunger is configured to move the stopper towards the distal end of the container, to expel primary fluid from the container through the distal end opening; and
 wherein the plunger is configured to expel secondary fluid from the at least one secondary fluid chamber towards the distal end opening, to expel at least a portion of a residual volume of primary fluid through the distal end opening.

According to at least one embodiment, there is provided a plunger system, the plunger system comprising:
  a stopper; and
  a plunger engageable with the stopper and configured to apply a force to the stopper,
  wherein stopper comprises at least one fluid chamber configured to contain a fluid; and
  wherein the plunger is configured to expel fluid from the at least one fluid chamber.

According to at least one embodiment, there is provided a plunger assembly for a syringe, the plunger assembly comprising:
  a stopper configured to be movably arranged within a container of the syringe; and
  a plunger engaged with the stopper and configured to apply a force to the stopper to move the stopper within the container,
  wherein the container is configured for containing a primary fluid, the container comprising a proximal end and a distal end and having a distal end opening at the distal end,
  wherein the plunger assembly comprises at least one secondary fluid chamber configured to contain a secondary fluid;
  wherein the plunger is configured to move the stopper towards the distal end of the container, to expel primary fluid from the container through the distal end opening; and
  wherein the plunger is configured to expel secondary fluid from the at least one secondary fluid chamber towards the distal end opening, to expel at least a portion of a residual volume of primary fluid through the distal end opening.

According to at least one embodiment, there is provided a plunger assembly, the plunger assembly comprising:
  a stopper; and
  a plunger engaged with the stopper and configured to apply a force to the stopper,
  wherein stopper comprises at least one fluid chamber configured to contain a fluid; and
  wherein the plunger is configured to expel fluid from the at least one fluid chamber.

According to at least one embodiment, there is provided a stopper comprising at least one fluid chamber configured to contain a fluid, wherein the stopper is configured to be engaged by a plunger to apply a force to the stopper and to expel fluid from the at least one fluid chamber.

According to at least one embodiment, there is provided a plunger configured for engagement with a stopper, the stopper having at least one fluid chamber configured to contain a fluid, wherein the plunger is configured to apply a force to the stopper and to expel fluid from the at least one fluid chamber.

According to at least one embodiment of the present disclosure, there is provided a syringe comprising:
  a container for containing a primary fluid;
  means for expelling primary fluid from the container; and
  means for expelling at least a portion of a residual volume of primary fluid from the container.

According to at least one embodiment of the present disclosure, there is provided a syringe comprising:
  a container for containing a primary fluid, the container comprising a proximal end and a distal end and having a distal end opening at the distal end;
  means for expelling primary fluid from the container through the distal end opening; and
  means for expelling at least a portion of a residual volume of primary fluid through the distal end opening.

According to at least one embodiment of the present disclosure, there is provided a syringe comprising:
  a container for containing a primary fluid, the container comprising a proximal end and a distal end and having a distal end opening at the distal end, the container further comprising at least one secondary fluid chamber configured to contain a secondary fluid;
  means for expelling primary fluid from the container through the distal end opening; and
  means for expelling secondary fluid from the at least one secondary fluid chamber, thereby to expel at least a portion of a residual volume of primary fluid through the distal end opening.

The singular forms "a", "an" and "the" include plural referents unless the context clearly dictates otherwise.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The disclosure is provided in relation to several embodiments that may share common characteristics and features. It is to be understood that one or more features of one embodiment may be combined with one or more features of other embodiments. In addition, a single feature or combination of features in certain of the embodiments may constitute additional embodiments. Specific structural and functional details disclosed herein are not to be interpreted as limiting but merely as a representative basis for teaching one skilled in the art to variously employ the disclosed embodiments and variations of those embodiments.

The subject headings used in this disclosures are included for the reader's ease of reference and should not be used to limit the subject matter found throughout the disclosure or the claims. The subject headings should not be used in construing the scope of the claims or the claim limitations.

BRIEF DESCRIPTION OF DRAWINGS

By way of example only, embodiments are now described with reference to the accompanying drawings, in which:

FIG. 6A is a partial cross-sectional view of a syringe according to at least one embodiment of the present disclosure, including a stopper having a plurality of ribs;

FIG. 6B is a partial cross-sectional view of the syringe of FIG. 6A showing the ribs in a compressed configuration;

FIG. 6C is a bottom view of the stopper of the syringe of FIG. 6A;

FIG. 12B is a side view of a plunger assembly of the syringe of FIG. 12A;

FIG. 12C is a partial cross-sectional side view of the plunger assembly of FIG. 12B;

DETAILED DESCRIPTION

Figure 1A:
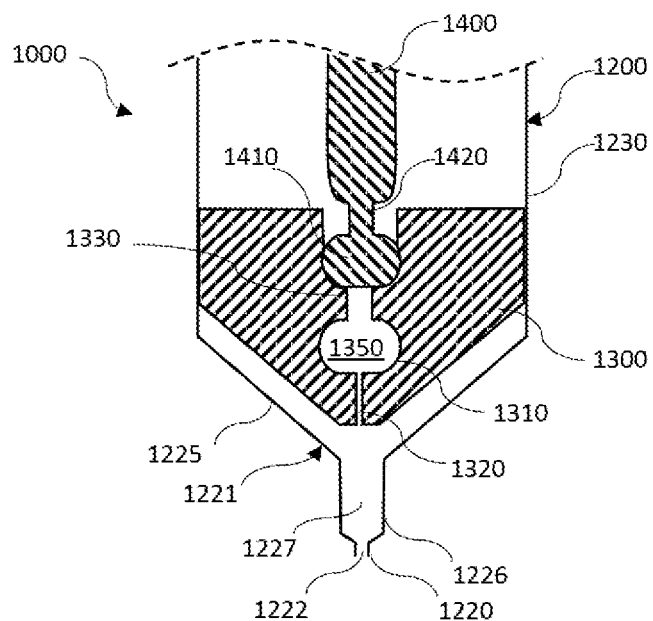
FIG. 1A is a partial cross-sectional view of a syringe according to at least one embodiment of the present disclosure, with a plunger of the syringe in a first engagement position.

Syringes according to certain embodiments of the present disclosure comprise a container, a stopper movably arranged within the container, and a plunger engageable with the stopper and configured to apply a force to the stopper to move the stopper within the container towards a distal end of the container. The syringe comprises at least one secondary fluid chamber configured to contain a secondary fluid.

In certain embodiments, the plunger is further configured to expel secondary fluid from the at least one secondary fluid chamber towards a distal end opening, to expel at least a portion of a residual volume of primary fluid through the distal end opening.

In at least one embodiment, the plunger is further configured to expel secondary fluid from the at least one secondary fluid chamber towards a distal end opening, to expel at least a portion of a residual volume of primary fluid through the distal end opening. For example, at least 99%, 98%, 96%, 95%, 90%, 80%, or 70% of the residual volume may be expelled.

In at least one embodiment, the syringe may be considered to have a double action: the first action being the plunger moving the stopper within the container towards the distal end, effecting an expulsion of primary fluid from the container through the distal end opening, and the second action being the plunger effecting an expulsion of secondary fluid from the at least one secondary fluid chamber towards the distal end opening, to expel at least a portion of a residual volume of primary fluid through the distal end opening.

In at least one embodiment, the container, when filled, may contain the majority of the fluid to be injected. For example, the container may contain a liquid medicament. However, other liquids are also contemplated. The container may be elongate, extending from a proximal end to a distal end. The container may comprise at least one side wall extending in an axial direction of the container. In at least one embodiment, the container may be substantially cylindrical. However, other shapes of the container are also contemplated. For example, the container may include a square, rectangular, triangular, oval or irregular shaped cross-sectional profile.

In at least one embodiment, the container may include an inner distal end surface. For example, the container may have a distal end section including at least one end wall extending radially inwards from the at least one side wall. The inner distal end surface may be a proximally facing surface of the at least one end wall. The at least one end wall may have a frusto-conical shape. However, other shapes of the at least one end wall are also contemplated. In other embodiments, the at least one end wall may extend substantially orthogonal to the axial direction of the container.

In at least one embodiment, the distal end section of the container may comprise a syringe tip. The distal end opening of the container may be at a distal end of the syringe tip. The syringe tip may define a syringe tip chamber, positioned distally of the stopper. The at least one end wall may have an outer edge connected to the at least one side wall and an inner edge connected to the syringe tip, the syringe tip projecting distally from the at least one side wall. Secondary fluid may be expelled from the at least one secondary fluid chamber into the syringe tip chamber.

The syringe tip may be adapted for mounting of a needle hub thereon. In at least one embodiment, the syringe tip may be configured to receive a needle hub by a press-fit connection. However, other configurations of the syringe tip are also contemplated. For example, in at least one embodiment, the syringe tip may comprise a threaded portion configured to engage a needle hub. For example, the syringe tip may comprise a Luer connection element adapted for connection to a corresponding Luer needle connection. In at least one embodiment, the syringe tip may be adapted for a press-fit connection; for example, the syringe tip may comprise a frustoconical section configured to engage a correspondingly shaped section of the needle hub. In at least one embodiment, a needle hub may be fixed to the syringe or integrally formed with the syringe tip.

In at least one embodiment, the container may comprise a standardised syringe barrel. The plunger and stopper may be adapted for use with standard (or common) syringe barrel types and/or sizes. The plunger and stopper may be provided as separate components, or engaged to form a plunger assembly, separate from the container. The plunger and stopper may be combined with the container to form the syringe.

The stopper may be slidably receivable (or received) in the container and axially movable within the container to expel primary fluid from the container through the distal end opening. In at least one embodiment, the stopper may be movable in a proximal direction and a distal direction within the container.

The stopper may be configured to be close-fittingly received within the container. The stopper may seal, or substantially seal, against an inner surface of the container. That is, the stopper may abut an inner surface of the container side wall for fluid-tight, or substantially fluid-tight, engagement therewith. The stopper may be substantially cylindrical in shape, extending longitudinally from a proximal end to a distal end and having an outer surface and an outside diameter. The stopper may be at least partially formed from a pliable, or resiliently deformable material, such as rubber, for example. However, other stopper materials are also contemplated.

At least a distal portion of the outer surface of the stopper may be shaped to correspond substantially to the distal end section and/or the at least one end wall of the container. For example, the container may have a conically tapered end wall and the stopper may have a correspondingly shaped frusto-conical projection at its distal end.

In at least one embodiment, the at least one secondary fluid chamber may be comprised in the stopper. The stopper may comprise one or more walls which define the at least one secondary fluid chamber. For example, the at least one secondary fluid chamber may comprise an inner void or cavity within the stopper, substantially surrounded by material of the stopper. In at least one embodiment, the stopper may comprise hydrophobic material to inhibit ingress of the primary fluid through the stopper into the at least one secondary fluid chamber.

In at least one embodiment, one or more walls of the stopper may define the at least one secondary fluid chamber in combination with one or more walls of the container. For example, the at least one secondary fluid chamber may be defined between an inner surface of a wall of the container and one or more outer walls of the stopper. In at least one embodiments, the stopper may comprise at least one recessed surface, wherein the at least one secondary fluid chamber may be defined between the at least one recessed surface and the interior surface of the wall of the container. In at least one embodiment, the at least one secondary fluid chamber is defined between deformable projections, such as ribs, spikes, or bumps, on an outer wall of the stopper. The projections may be configured to trap secondary fluid therebetween. In at least one embodiment, the stopper may comprise a plurality of ribs on a distal facing surface, the chambers configured to contain secondary fluid being defined between adjacent ribs. In at least one embodiment, the secondary fluid chambers may be defined between the ribs and an interior surface of the container. The ribs may be deformable, such that, when the stopper reaches a distal stop position in the container, the ribs are compressed against the distal end wall of the container. Compression of the ribs may result in a reduction in size of the secondary fluid chambers and corresponding compression of the secondary fluid contained in chambers, such that the secondary fluid is expelled through the fluid flow paths towards the distal end opening of the container. In other embodiments, in addition to or as an alternative to the recessed surface or deformable projections, the stopper may include a compressible porous material, such as a sponge material. The compressible porous material may be hydrophobic. In some embodiments, the ribs may be formed from the compressible porous material.

In at least one embodiment, a substantial portion of the stopper (or in some embodiments, the entirety of the stopper) may be formed from the compressible porous, material. The compressible porous material may have a graded porosity. For example, the sponge material may be denser, stiffer and/or less compressible at or adjacent to a proximal end of the stopper, while the material at a distal end of the stopper may have an increased compressibility. The porous material of the stopper may define a plurality of secondary fluid containing chambers, or a network of chambers, configured to contain the secondary fluid. For example, the porous material may entrap air (or other secondary fluid) therein. The air may be expelled upon compression of the porous material, against the distal end wall of the container when the stopper reaches a distal stop position in the container, for example.

In at least one embodiment, an outer surface of the stopper may be oversized in comparison to the distal end section of the container. In such embodiments, entry of the stopper into the distal end section of the container may compress the stopper. Where the at least one secondary fluid chamber may be comprised in or defined by the stopper, compression of the stopper as it enters the distal end section of the container may cause a reduction in size of the at least one secondary fluid chamber, thereby expelling secondary fluid from the at least one secondary fluid chamber.

The stopper may be configured to be engageable by a distal end, or head, of the plunger. The stopper may include a proximal connecting portion for connecting to the distal end of the plunger. In at least one embodiment, the stopper may comprise a female connecting element adapted to connect to a male connecting element of the plunger. In other embodiments, the stopper may comprise a male connecting element adapted for connection to a female connecting element of the plunger.

In at least one embodiment, the connecting portion of the stopper may include at least one protrusion configured to engage a portion of plunger to couple the plunger to the stopper. In at least one embodiment, a head portion of the plunger may be releasably coupled to the stopper. The protrusion may include, for example, locking arms, an undercut portion, a flared portion, a shoulder portion. In at least one embodiment, the protrusion may be configured to engage the plunger head in a snap-fit connection. In other embodiments, the stopper may be configured to be engageable by the plunger without the plunger coupling thereto.

In at least one embodiment, the stopper may comprise at least one fluid flow path for secondary fluid to exit the secondary fluid chamber. The fluid flow path may enable fluid communication between the at least one secondary fluid chamber and the distal end opening of the container, such that the secondary fluid moves through the fluid flow path as it is expelled from the at least one secondary fluid chamber towards the distal end opening. The fluid flow path may be, for example, a channel or bore through material of the stopper. Alternatively, the fluid flow path may be comprised in porous material. The porous material may create multiple interlinked channels, or parallel channels. In at least one embodiment, the fluid flow path may be realised (or created) by pressure in the secondary chamber splitting the material of the stopper. The stopper material may be configured to split to create the fluid flow path at a predetermined pressure.

In at least one embodiment, the fluid flow path may have a width or diameter configured to inhibit (or substantially inhibit) capillary action, that is, such that adhesive forces between the fluid and stopper material are stronger than cohesive forces between the fluid molecules. The fluid flow path may be configured to inhibit capillary action of primary fluid from the container into the at least one secondary fluid chamber containing the secondary fluid. In at least one embodiment, at least a portion of the stopper material may be configured to inhibit (or substantially inhibit) capillary action in the fluid flow path; for example, at least a portion of the stopper may comprise a hydrophobic material.

In at least one embodiments, a distal portion of the fluid flow path may have a reduced dimension, such as a narrowed width or diameter, compared to a proximal region of the fluid flow path. The proximal region of the fluid flow path, adjacent the at least one secondary fluid chamber, may accordingly have a greater dimension than the distal portion of the fluid flow path, for example having an increased width or diameter. The narrowed distal portion of the fluid flow path may be expandable. For example, the narrowed distal portion may expand under pressure to allow secondary fluid to exit the at least one secondary fluid chamber. In at least one embodiment, the fluid flow path may be configured to expand in response to a change in shape of the stopper; for example, the stopper may be configured to be deformable to expand the fluid flow path. The stopper may be configured to be compressible or otherwise deformable when at the distal stop position, for example by compression of the stopper against a distal end wall of the container and/or by the entering of the stopper into a narrowed distal end section of the container. Additionally or alternatively, the stopper may be configured to be deformed to expand the fluid flow path by application of force from the plunger.

In at least one embodiment, the fluid flow paths may configured to direct secondary fluid into the syringe tip chamber in a flow pattern which creates a venturi, or mass effect, by their motion. For example, the fluid flow paths may be configured to direct secondary fluid into the syringe tip chamber at an angle such that a circular flow is created within the syringe tip chamber, producing vortex flow. Vortex flow may enhance entrainment of the primary fluid residuum and promote ejection of the primary fluid residuum rather than mixing of the primary and secondary fluids.

In at least one embodiment, for example, where the at least one secondary fluid chamber is defined between an exterior surface of the stopper and an inner wall of the secondary fluid chamber, the fluid flow path may be a channel defined in an exterior surface of the stopper between the secondary fluid chamber and a distal end of the stopper.

In at least one embodiment, a fluid flow path may be created in the stopper by the stopper striking a penetrating member (such as a pin, spike or other sharp protruding element) at a distal end of the container. The penetrating member may be configured to penetrate the stopper to create a fluid flow path for secondary fluid to exit the at least one inner chamber. The penetrating member may be vented. For example, the penetrating member may have at least one wall defining an internal lumen. The at least one wall may include at least one opening or fenestration. The lumen and opening may together define the fluid flow path.

In at least one embodiment, the plunger may be configured to engage the stopper to move the stopper axially in a distal direction to drive fluid out of the container, or in a proximal direction to draw fluid into the container. In other embodiments, the plunger may be configured to engage the stopper to move the stopper in a distal direction, toward the distal end outlet, but not in a proximal direction.

In at least one embodiment, the plunger may be movably engageable with the stopper between a first engagement position and a second engagement position. When the plunger is in the first engagement position, the plunger may be configured to move the stopper towards the distal end of the container to expel primary fluid from the distal end opening. When the plunger moves from the first engagement position to the second engagement position, secondary fluid may be expelled from the at least one secondary fluid chamber of the stopper through the fluid flow path and towards the distal end opening.

In at least one embodiment, when the plunger moves from the first engagement position to the second engagement position, at least a portion of the plunger may enter into a chamber in the stopper. For example, the head of the plunger may enter into a chamber in the stopper. The chamber that the plunger enters into may be the at least one secondary fluid chamber. In such embodiments, portion of the plunger that enters into the at least one secondary fluid chamber may directly displace secondary fluid in the secondary fluid chamber so that the displaced secondary fluid is expelled through the fluid flow path and towards the distal end opening.

In at least one embodiment, the plunger enters into a rod receiving chamber that is different from the at least one secondary fluid chamber. For example, when the plunger moves from the first engagement position to the second engagement position, the at least a portion of the plunger that enters into the rod receiving chamber may cause displacement of one or more of the stopper walls, such that the secondary fluid chamber is reduced in size and secondary fluid is expelled from the secondary fluid chamber through the fluid flow path and towards the distal end opening. In such embodiments, movement of the plunger from the first engagement position to the second engagement position increases the pressure in the at least one secondary fluid chamber, at least partially expelling the contents of the at least one secondary fluid chamber.

In other embodiments, the plunger may compress the stopper. In some such embodiments, the plunger may not enter a chamber of the stopper. For example, when the plunger moves from the first engagement position to the second engagement position, the plunger may cause displacement of one or more of the stopper walls of the stopper, such that the at least one secondary fluid chamber is reduced in size. Reduction in size of the secondary fluid chamber may increase pressure in the at least one secondary fluid chamber, such that secondary fluid may be expelled from the secondary fluid chamber through the fluid flow path and towards the distal end opening.

In at least one embodiment, the stopper may comprise at least one deformable member configured to resist movement of the plunger from the first engagement position to the second engagement position. The force applied to the stopper to move the stopper within the container may be configured to be less than a force applied to the plunger to move the plunger from the first engagement position to the second engagement position. For example, the plunger may overcome a resistance before moving from the first engagement position to the second engagement position. The force required to overcome the resistance may be greater than the force required to move the stopper within the container. That is, the force required to overcome the resistance may be greater than the frictional resistance force between the stopper and the container wall and the resistance provided by the primary fluid (which may be greater during injection into, for instance, muscle, than upon simply expelling the primary fluid without injection). In some embodiments, the deformable member may be resiliently deformable or at least partially resiliently deformable. As used herein, resiliently deformable means that the deformable member may change shape under application of a force acting on the deformable member and may resume its initial shape upon release of the force. In other embodiments, movement of the plunger from the first position to the second engagement position may permanently deform the deformable member or permanently deform at least in part the deformable member. As used herein, permanently deform means that the deformable member may change shape under application of a force acting on the deformable member and may wholly or partially retain its changed shape upon release of the force. The plunger may be configured to move from the first engagement position to the second engagement position after the stopper reaches a distal stop position within the container. The stopper may be considered to have reached the distal stop position when the stopper abuts an inner distal end surface of the container, for example.

In at least one embodiment, the plunger may engage the deformable member to move the stopper within the container. In some embodiments, the deformable member is engageable to move the stopper in both distal and proximal directions within the container. In some embodiments, the deformable member is configured to permanently deform, such that the stopper may no longer be withdrawn by the plunger after movement of the plunger from the first position to the second engagement position.

In at least one embodiment, the plunger may be configured to snap fit into the second engagement position. In such embodiments, the deformable member may comprise at least one protrusion configured to snap-fittingly engage the plunger. For example, the deformable member may be a radially inwardly extending shoulder. A flexibility of the protrusion may be configured to provide a predetermined resistive force, which is configured to be greater than the force required to move the stopper within the container.

In at least one embodiment, the primary fluid may comprise a liquid medicament and the secondary fluid may comprise a gas. In other embodiments, the secondary fluid may comprise a liquid. For example, the secondary fluid may comprise air or saline. In at least one embodiment, the secondary fluid may comprise a liquid medicament. The secondary fluid may be selected to be compatible with a minimum diameter of a needle cannula attached (or attachable) to the syringe (that is, able to flow through the needle cannula).

In at least one embodiment, the secondary fluid may be a hydrogel. The secondary fluid may be a thermo-setting hydrogel. In at least one embodiment, the hydrogel secondary fluid may provide inhibit dilution of the primary fluid by surrounding tissues and fluids. Additionally or alternatively, the hydrogel secondary fluid may elute nutrients.

In some embodiments, the primary fluid may comprise a chemical and the secondary fluid may be configured to react with the chemical in the primary fluid to activate one or more properties of the combined fluids. In other embodiments, the secondary fluid may be configured to react with a third substance, such as a metal or a substance within the subject's body. The reaction may include for example, polymerisation, activation of light sensitivity or may be configured to seal the injection site. In at least one embodiment, the reaction may result in expansion of the fluids, for example by creation of one or more gasses.

In at least one embodiment, the secondary fluid may be heated or chilled. That is, the secondary fluid may be configured to be warmer or cooler than the primary fluid. In at least one embodiment, the secondary fluid may comprise a thixotropic fluid. A thixotropic secondary fluid may be configured to acts as a stopper upon cessation of fluid flow. The secondary fluid may include a signalling element for identifying the injection site or signalling expulsion of the primary and/or secondary fluids.

In at least one embodiment, a volume of the secondary fluid expelled from the at least one secondary fluid chamber may be configured to be at least substantially equal to the residual volume of primary fluid. For example, the volume of secondary fluid expelled from the at least one secondary fluid chamber may be about 90%, about 95%, about 97%, about 98%, about 99%, about 100%, about 101%, about 102%, about 103% about 105%, or about 110% of the residual volume of the primary fluid. For example, the volume of secondary fluid expelled from the at least one secondary fluid chamber may be 90%, 95%, 100% or 105% of the residual volume of the primary fluid. This may be the case in at least one embodiment where the secondary fluid is substantially non-compressible (for example, where the secondary fluid is a liquid). In some embodiments, the volume of secondary fluid may be greater than the residual volume of primary fluid. For example, the volume of secondary fluid expelled from the at least one secondary fluid chamber may be at least 110%, at least 120%, at least 150%, at least 160%, at least 170%, at least 180%, at least 190% at least 200% or more of the residual volume of the primary fluid. Where the secondary fluid is compressible, the volume of the secondary fluid may be greater than the residual volume of primary fluid, such that, when the secondary fluid is compressed, its volume is not reduced beyond that of the residual primary fluid. In at least one other embodiment, the volume of secondary fluid expelled from the at least one secondary fluid chamber may be many times greater than the residual volume of the primary fluid. For example, the volume of secondary fluid expelled from the at least one secondary fluid chamber may be at least 200%, 300%, 400%, 500% or more of the residual volume of the primary fluid.

In at least one embodiment, the volume of the secondary fluid may be configured such that the secondary fluid expels at least a portion of the residual primary fluid, but substantially no secondary fluid is expelled from the container. In other embodiments, the volume of the secondary fluid may be configured such that a predetermined amount of the secondary fluid is expelled from the distal end opening of the container and/or a distal end of an attached needle cannula. For example, it may be desirable to inject a quantity of secondary fluid after injection of the primary fluid. The predetermined amount of the secondary fluid may be up to about 1%, about 2%, about 3%, about 4%, about 5%, about 10%, about 20%, about 30%, about 40%, about 50%, about 60%, about 70%, about 80%, about 90%, about 95%, or about 100% of a total volume of the secondary fluid. For example, the predetermined amount of the secondary fluid may be 1%, 5%, 10%, 50%, 80%, 90% or 95% of a total volume of the secondary fluid. Injection of secondary fluid may be useful, for example, for indicating that injection has been performed and/or that the primary fluid was injected. In at least one embodiment, the volume of secondary fluid may be configured such that the expelled volume of secondary fluid is less than the expelled volume of primary fluid. In at least one embodiment, the volume of secondary fluid may be configured such that the expelled volume of secondary fluid is greater than the expelled volume of primary fluid. In at least one embodiment, the volume of secondary fluid may be configured such that the expelled volume of secondary fluid is substantially equal to (that is between about 90% and about 110% of, for example, 100% of) the expelled volume of primary fluid.

In at least one embodiment, the syringe may comprise a penetrating member within the container, at or adjacent to the distal end. The penetrating member may extend into the container from the at least one end wall. The penetrating member may comprise at least one side wall defining an internal lumen and at least one opening in the side wall, the lumen and opening defining the fluid flow path. The penetrating member may be configured to penetrate the stopper to create a fluid flow path for secondary fluid to exit the at least one secondary fluid chamber. In such embodiments, the container may comprise at least one side wall extending in an axial direction of the container and a distal end section including at least one end wall extending radially inwards from the at least one side wall.

In at least one embodiment, the at least one secondary fluid chamber may be comprised in the plunger. In some embodiments, the plunger may comprise a primary shaft having at least one wall defining the at least one secondary fluid chamber. In some embodiments, the at least one secondary fluid chamber may be comprised in an interior lumen of the primary shaft. In at least one embodiment, the plunger the at least one wall of the primary shaft may be compressible or collapsible. The at least one wall of the primary shaft may be configured to collapse to reduce the size of the secondary fluid chamber to expel secondary fluid from the at least one secondary fluid chamber. The at least one wall of the primary shaft may be configured to collapse when or after the stopper reaches the distal stop position within the container, for example.

In other embodiments, the plunger may comprise a secondary shaft axially slidably receivable in the interior lumen of the primary shaft. The secondary plunger shaft may be movable towards a distal end of the primary plunger shaft to expel secondary fluid from the at least one secondary fluid chamber.

In at least one embodiment, the plunger may comprise a seal within the lumen of the primary shaft. The seal and the lumen may together define the at least one secondary fluid chamber. The seal may comprise, for example, a valve, a penetrable membrane, a flap, or other suitable sealing mechanism. In at least one embodiment, the seal may additionally or alternatively comprise a thermally unstable, chemically unstable or otherwise unstable material, which may be broken down upon exposure to the secondary fluid. In at least one embodiment. The primary shaft may comprise a fitting at or adjacent to its proximal end, the fitting adapted to fluidly couple a secondary syringe to the lumen. In such embodiments, the seal may configured to be penetrated, broken or otherwise opened by the secondary syringe such that the secondary syringe is in fluid communication with the at least one secondary fluid chamber. Ejection of fluid (such as an additional volume of secondary fluid or a volume of a tertiary fluid) from the secondary syringe may drive the secondary fluid out of the at least one secondary fluid chamber and through the fluid flow path toward the distal end opening of the container.

Figure 1B:
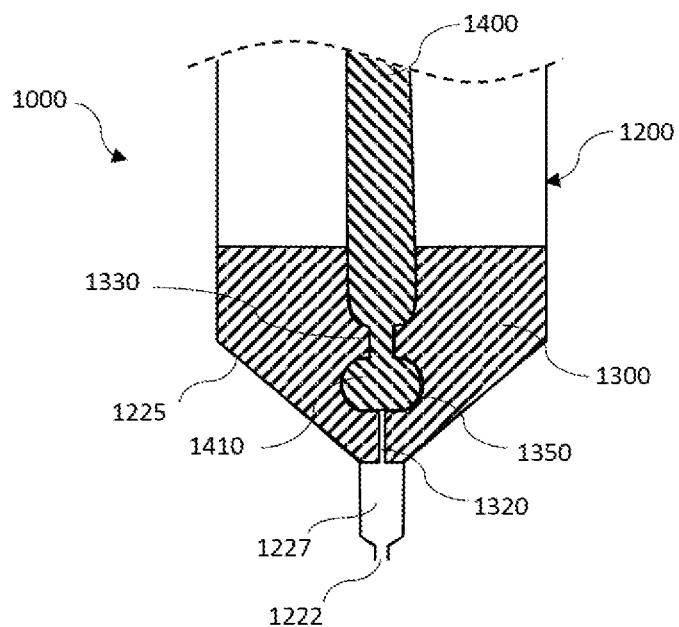
FIG. 1B is a partial cross-sectional view of the syringe of FIG. 1A, with the plunger in a second engagement position.

Cross-sectional diagrams of a syringe 1000 according to at least one embodiment of the present disclosure are shown in FIGS. 1A and 1B. The syringe 1000 comprises a container 1200 configured to contain a primary fluid. The container 1200 comprises a side wall 1230 extending in an axial direction of the container 1200 from a proximal end to a distal end 1220. A distal end section 1221 of the container 1200 includes an end wall 1225 extending radially inwards from the side wall 1230. In the exemplary embodiment, the distal end wall 1225 extends distally as well as radially inwardly, defining a frusto-conical shaped distal end section 1221.

The distal end section 1221 comprises a syringe tip 1226 defining a syringe tip chamber 1227. The end wall 1225 has an outer edge connected to the side wall 1230 and an inner edge connected to the syringe tip 1226, the syringe tip 1226 projecting distally from the side wall 1230 and terminating in a distal end opening 1222.

The syringe tip 1226 may be adapted for mounting of a needle hub thereon. In some embodiments, the syringe tip 1226 may be configured to receive a needle hub by a press-fit connection. In other embodiments, the syringe tip 1226 may comprise a threaded portion configured to engage a needle hub. For example, the syringe tip 1226 may comprise a Luer connection element adapted for connection to a corresponding Luer needle connection.

In at least one embodiment herein, the stopper 1300 typically may be formed from a resiliently deformable material and may be configured to be close-fittingly received within the container 1200 to form a fluid-tight engagement therewith. That is, the stopper may abut an inner surface of the wall of the container such that fluid is inhibited (or substantially inhibited) from passing the stopper. A distal region of the stopper 1300 may be shaped to conform to the distal end wall 1225 of the container 1200. In the exemplary embodiment, the distal portion of the stopper 1300 has a frusto-conical shape corresponding to the frusto-conically shaped distal end section 1221 of the container 1200.

The stopper 1300 defines an inner, secondary fluid chamber 1350 configured to contain a secondary fluid. The inner chamber 1350 may be defined by an internal wall 1310 of the stopper, which substantially surrounds the secondary fluid chamber 1350. A bore provides a fluid flow path 1320 extending distally through material of the stopper 1300 from the inner chamber 1350 to allow secondary fluid to flow out of the inner chamber 1350, and the stopper 1300, towards the distal end opening 1222.

In this and other embodiments herein, the plunger 1400 may be configured to engage the stopper 1300 to apply a force to the stopper 1300 to move the stopper 1300 axially within the container 1200 towards the distal end 1220 to expel primary fluid through the distal end opening 1222. The plunger may have a finger grip, or other form of handle facilitating gripping by a user, at a proximal end. The plunger and stopper may be configured to be pre-assembled together and fitted into the container 1200 prior to packaging and sterilisation.

In at least one embodiment, the plunger may be configured for engagement with a driving device to provide the force required to move the plunger. The driving device may comprise an automated injection device or energy assisted injection device, for example. The plunger may additionally or alternatively comprise detection and/or signalling means for communicating to an external or internal sensor. The information may include, for example, force data, position data and/or pressure data. The information may relate to syringe status, injection progress and/or secondary chamber activation status. The plunger may also include, or be operatively associated with, a remote activation mechanism.

The plunger 1400 may be movably engageable with the stopper 1300 between a first engagement position as shown in FIG. 1A and a second engagement position as shown in FIG. 1B. When the plunger 1400 is in the first engagement position, a head 1410 of the plunger engages a radially inwardly extending shoulder protrusion 1330 of the stopper 1300 which resists movement of the plunger 1400 from the first engagement position to the second engagement position. In the first engagement position, force applied to the plunger 1400 moves the stopper 1300 towards the distal end 1220 of the container 1200 to expel primary fluid from the distal end opening 1222.

The plunger 1400 advances the stopper 1300 axially within the container 1200 in a distal direction, expelling primary fluid through the distal end opening 1222, until the stopper 1300 reaches a distal stop position within the container 1200 in which the stopper 1300 abuts a distal end surface of the container 1200, which may be a proximally facing surface of the distal end wall 1225 as shown in FIG. 1B. In alternative embodiments, the syringe may comprise an alternative stop member, such as a projection or resisting element positioned proximal of the distal end wall. The stop member may be configured to resist the motion of the plunger and may define a distal stop position. When the stopper 1300 reaches the distal stop position, a residual volume (residuum) of primary fluid may remain in the syringe, such as in the tip chamber 1227 and/or in an attached needle cannula distal of the stopper 1300.

In the exemplary embodiment shown in FIGS. 1A and 1B, the shoulder protrusion 1330 may be resiliently deformable. Once the stopper 1300 reaches the distal stop position, further force may be applied to the plunger 1400 to overcome the resistance of the shoulder protrusion 1330, such that the plunger 1400 advances from the first engagement position to the second engagement position. In the second engagement position, the head 1410 of the plunger 1400 enters into the inner chamber 1350 of the stopper 1300. The head 1410 of the plunger directly displaces the secondary fluid contained in the inner chamber 1350. The displaced secondary fluid may be expelled through the fluid flow path 1320 and into the syringe tip chamber 1227 towards the distal end opening 1222 of the syringe 1000.

In the exemplary embodiment of FIGS. 1A and 1B, the plunger includes a narrowed neck portion 1420 located proximally of the head 1410 and configured to be snap-fittingly engaged by the shoulder protrusion 1330 once in the second engagement position.

In at least one embodiment described herein, the force applied via the plunger to move the stopper within the container may be configured to be less than a force applied to the plunger to move the plunger from the first engagement position to the second engagement position, by overcoming resistance of the shoulder protrusion 1330, for example. The plunger may thus be prevented from moving from the first engagement position to the second engagement position until completion of the first action when the stopper is at the distal stop position.

In at least one embodiment, a volume of the secondary fluid expelled from the inner chamber 1350 may be substantially equal to the residual volume of primary fluid. For example, the volume of secondary fluid may be equal to the volume of primary fluid contained in the syringe tip chamber 1227 and, optionally, in an attached needle cannula. In some embodiments, the expelled volume of secondary fluid may be greater than the residual volume of primary fluid. The volume of secondary fluid may be configured (or at least partially configured), for example, to account for compression of the secondary fluid and/or the primary fluid during expulsion of the respective fluids. For example, where the primary fluid is a liquid and the secondary fluid is a gas, an uncompressed volume of the secondary fluid may be greater than the volume of residual primary fluid such that when the gas is compressed during ejection, the compressed volume of remains larger than the volume of primary fluid. The volume of secondary fluid may generally be configured such that a substantial portion of the residual volume of primary fluid may be expelled through the distal end opening 1222 and/or through a distal end of an attached needle cannula for injection. As used herein a substantial portion means at least 90%, 94%, 95%, 96%, or 98%. For example, in some embodiments, the volume of secondary fluid may be configured to effect expulsion of at least 5%, at least 10%, at least 20%, at least 30%, at least 40%, at least 50%, at least 60%, at least 70%, at least 80%, at least 90%, at least 95%, at least 96%, at least 97%, at least 98%, at least 99% or more of the residual volume of primary fluid. In some embodiments, the volume of secondary fluid may be configured such that a quantity of secondary fluid is also expelled for injection.

A volume of the at least one secondary fluid chamber may be configured to be substantially equal to the expelled volume of primary fluid. As used herein, substantially equal means about 90%, about 95%, about 97%, about 98%, about 99%, about 100%, about 101%, about 102%, about 103% about 105%, or about 110% of the residual volume of the primary fluid. For example, the volume of the at least one secondary fluid chamber may be configured to be 90%, 100% or 110% of the expelled volume of primary fluid. This may be the case, for example, in embodiments where a portion of the plunger enters and fills the secondary fluid chamber and directly displaces the secondary fluid therein. For example, in the exemplary embodiment shown in FIGS. 1A and 1B, the plunger head 1410 may be configured to fill a substantial portion of the secondary fluid chamber 1350 in the second engagement position, thus expelling a substantial portion of the secondary fluid contained in the secondary fluid chamber 1350 through the fluid flow path 1320 and towards the distal end opening 1222. In other embodiments, however, it will be appreciated that secondary fluid contained in the at least one secondary fluid chamber may not be expelled in its entirety from the at least one secondary fluid chamber. For example, in an alternative embodiment discussed below with reference to FIGS. 2A and 2B, secondary fluid chambers 2350 may be incompletely compressed, such that a volume of secondary fluid remains in the compressed chambers 2350 after the plunger has moved from the first engagement position to the second engagement position.

Figure 2A:
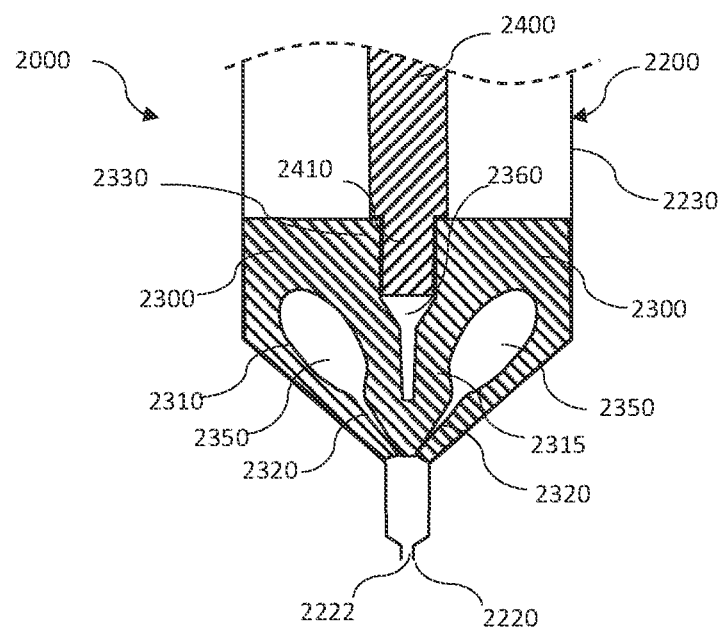
FIG. 2A is a partial cross-sectional view of a syringe according to at least one embodiment, of the present disclosure, with a plunger of the syringe in a first engagement position.
Figure 2B:
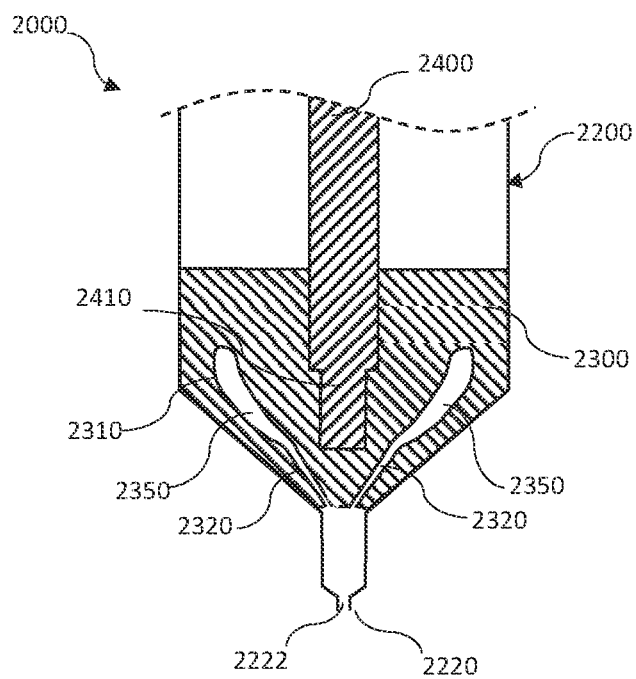
FIG. 2B is a partial cross-sectional view of the syringe of FIG. 2A, with the plunger in a second engagement position.

As indicated above, a syringe 2000 according to an alternative embodiment of the disclosure is illustrated in FIGS. 2A and 2B. The syringe 2000 includes a container 2200 extending from a proximal end to a distal end 2220 and having a distal end opening 2222, a stopper 2300 and a plunger 2400. In FIGS. 2A and 2B the stopper 2300 defines a plurality of inner, secondary fluid chambers 2350 configured to contain secondary fluid, and a rod receiving chamber 2360 configured to receive a head 2410 of the plunger 2400. The inner chambers 2350 and the rod receiving chamber 2360 may be defined by one or more walls 2310 of the stopper 2300 which substantially surround the chambers 2350, 2360. The stopper 2300 comprises fluid flow paths 2320 connected to one or more of the inner chambers 2350 for secondary fluid to exit the inner chambers 2350. Although in FIGS. 2A and 2B only two chambers 2350, more chambers 2350 may be present. Moreover, alternative embodiments may have only a single chamber.

In this exemplary embodiment, when the plunger 2400 moves from the first engagement position to the second engagement position, the head 2410 of the plunger 2400 enters into the rod receiving chamber 2360, which is different from the inner, secondary fluid chambers 2350. Movement of the plunger 2400 from the first engagement position to the second engagement position causes displacement of at least one deformable wall portion 2315 of the stopper walls 2310, such that the inner chambers 2350 may be compressed and reduced in size, as shown in FIG. 2B, expelling secondary fluid from the inner chambers 2350 through the fluid flow paths 2320 and towards the distal end opening 2222.

As shown in FIG. 2A, a distal portion of the fluid flow paths 2320 has a narrowed diameter, while a proximal region of the fluid flow paths 2320, adjacent to the secondary fluid chambers 2350, has a widened diameter. The narrowed distal portion of one or more fluid flow paths (for example, 2320) may expand under pressure to allow secondary fluid to exit the secondary fluid chambers 2350. The narrowed distal opening of one or more fluid flow paths (for example, 2320) may inhibit ingress, e.g., due to capillary action, of the primary fluid from the container 2200 into the secondary fluid chambers 2350, e.g., during the initial phase of expelling the primary fluid by movement of the stopper 2300 within the container 2200.

In this or other embodiments described herein, in addition to or as an alternative to narrowed distal openings, one or more fluid flow paths may comprise one or more valves, such as a flap valve or split valve, inhibiting ingress of the primary fluid into the secondary fluid chamber(s), e.g. during the initial phase of expelling the primary fluid by movement of the stopper within the container. The one or more narrowed distal openings and/or valves may be forced open by increased pressure from the secondary fluid, or by widening e.g., due to a distortion of the stopper, upon movement of the plunger from the first position to the second position. In some embodiments, the one or more narrowed distal openings and/or valves may be deformed, and closed, under the pressure of ejecting the primary fluid and subsequently opened under increased pressure from the secondary fluid once the primary fluid ejection is complete.

Figure 3A:
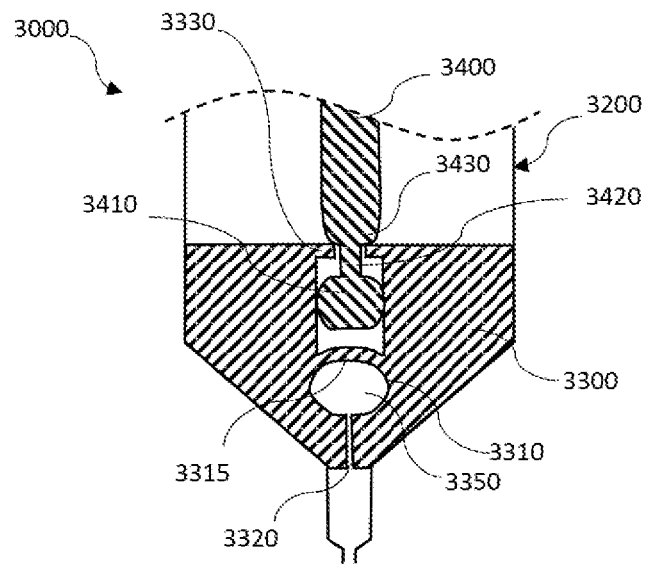
FIG. 3A is a partial cross-sectional view of a syringe according to at least one embodiment, of the present disclosure, with a plunger of the syringe in a first engagement position.
Figure 3B:
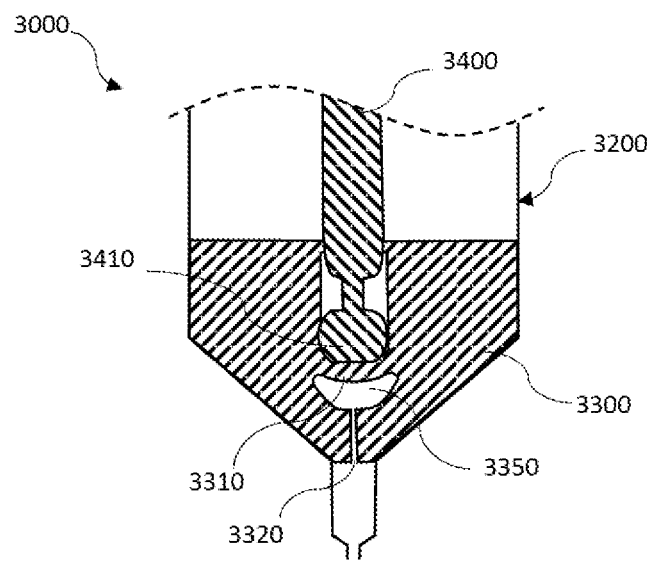
FIG. 3B is a partial cross-sectional view of the syringe of FIG. 3A, with the plunger in a second engagement position.

A syringe 3000 according to another embodiment of the disclosure is shown in FIGS. 3A and 3B. The syringe 3000 is similar to the syringe 1000 of FIGS. 1A and 1B as discussed above, In FIGS. 3A and 3B, the plunger 3400 is not configured to enter a secondary fluid chamber 3350. In this exemplary embodiment, the plunger 3400 may be engageable with the stopper 3300 in the first engagement position, as shown in FIG. 3A, by a deformable member of the stopper 3300 in the form of a radially inwardly extending shoulder 3330. The plunger 3400 has a neck portion 3420 having a reduced width and located between the plunger head 3410 and a shoulder 3430 of the plunger, and configured to be engaged by the shoulder 3330 of the stopper 3300. The shoulder 3430 of the plunger 3400 may be engageable with a proximal surface of the stopper shoulder 3330 to apply force to the stopper 3300 to move the stopper 3300 in the distal direction. Additionally, the plunger head 3410 may be engageable with a distal surface of the stopper shoulder 3330 to allow a force to be applied, in this embodiment, to move the stopper 3300 in a proximal direction, to draw fluid into the container 3200, for example.

In this exemplary embodiment, the stopper 3330 comprises a single inner, secondary fluid chamber 3350 configured to contain secondary fluid. The secondary fluid chamber 3350 may be defined by one or more walls 3310 of the stopper 3300, which substantially surround the secondary fluid chamber 3350, and which include at least one deformable wall portion 3315. In the first engagement position, as shown in FIG. 3A, the plunger 3400 may not be in contact with the deformable wall portion 3315. In alternative embodiments, the plunger may be in contact with, or even attached to, the deformable wall portion 3315, but configured to apply no force, or substantially no force, to the deformable wall portion when in the first engagement position. When the plunger 3400 overcomes the resistance of the stopper shoulder 3300 and moves into the second engagement position, the head 3410 may impinge on and deform the deformable wall portion 3315, compressing the secondary fluid chamber 3350 such that the secondary fluid chamber is reduced in size and secondary fluid is expelled through the fluid flow path 3320.

In this and other embodiments, a deformable member such as the shoulder 3330 may be permanently deformed upon movement of the plunger 3400 from the first engagement position to the second engagement position. For example, the deformable member, such as the stopper shoulder 3330, may be configured to deform such that, after movement of the plunger 3400 from the first engagement position to the second engagement position, the stopper 3300 may no longer be engaged by the plunger 3400 to be moved in the proximal direction. This may provide evidence of use, evidence of tampering and/or prevent re-use of the syringe 3000.

Figure 4A:
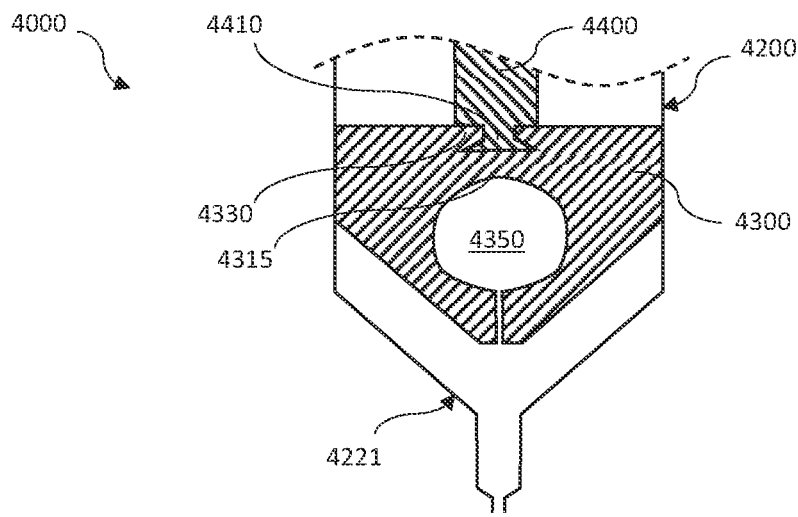
FIG. 4A is a partial cross-sectional view of a syringe according to at least one embodiment of the present disclosure.
Figure 4B:
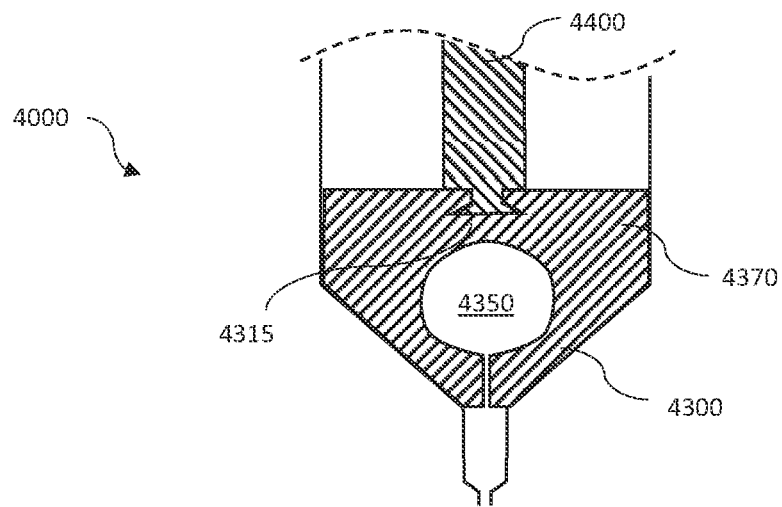
FIG. 4B is a partial cross-sectional view of the syringe of FIG. 4A, with a stopper in a distal stop position within a container of the syringe.
Figure 4C:
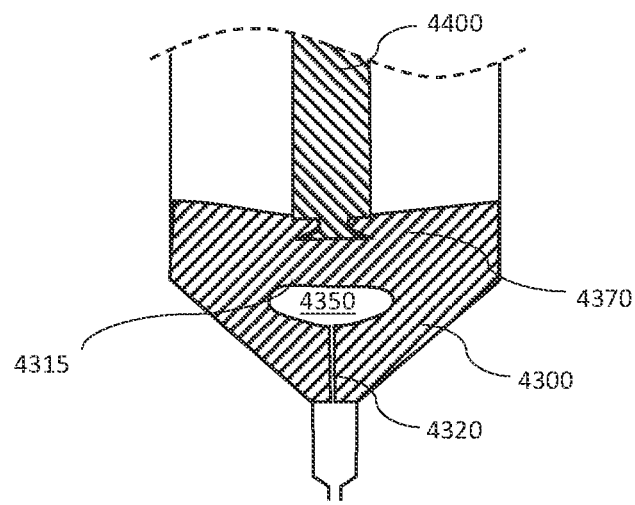
FIG. 4C is a partial cross-sectional view of the syringe of FIG. 4A with the stopper in a compressed configuration.

A syringe 4000 according to another embodiment of the present disclosure is shown in FIGS. 4A to 4C. The syringe 4000 is similar to the syringes 1000, 2000, 3000 of FIGS. 1A to 3B, as discussed above. In FIGS. 4A and 4C, the stopper 4300 does not comprise a chamber which receives a portion of the plunger 4400 when the plunger 4400 moves from the first engagement position to the second engagement position. Instead, when the plunger 4400 moves from the first engagement position (as shown in FIGS. 4A and 4B) to the second engagement position (as shown in FIG. 4C), the plunger 4400 may cause displacement of at least one deformable wall portion 4315 of the stopper 4300.

In this exemplary embodiment, the deformable wall portion 4315 may be provided at a proximal region 4370 of the stopper 4300. The force from the plunger 4400 that is required to substantially deform the deformable wall portion 4315 is greater than the force required from the plunger 4400 to move the stopper 4300 distally within the container 4200, prior to the stopper reaching a distal stop position. When the stopper 4300 reaches the distal stop position, further force applied to the stopper 4300 via the plunger 4400 causes displacement of the deformable wall portion 4315, and generally collapses the proximal region 4370, compressing the secondary fluid chamber 4350. As a result of the compression, the secondary fluid chamber 4350 may be reduced in size and secondary fluid may be expelled from the secondary fluid chamber 4350 through the fluid flow path 4320. The proximal region 4370 may remain substantially uncollapsed prior to the stopper 4300 reaching the distal stop position. Nevertheless, in at least this embodiment and in other such embodiments, the secondary fluid chamber 4350 and the secondary fluid contained therein may come under increased pressure during the first stage of primary fluid expulsion in which the stopper 4300 may be moved within the container. This increased pressure during the initial stage of primary fluid expulsion may inhibit ingress of the primary fluid into the secondary fluid chamber 4350 via the fluid flow path 4320.

In alternative embodiments, the stopper 4300 may additionally or alternatively comprise a collapsible region and/or deformable wall portion located at a distal portion of the stopper 4300. In such embodiments the compression of the distal collapsible region and/or deformation of the wall portion may be effected by the stopper entering and contacting the distal end section 4221 of the container 4200. For example, a distal portion of the stopper 4300 may be oversized in comparison to the distal end section of the container 4200. In such embodiments, entry of the stopper 4300 into the distal end section 4221 of the container 4200 may compress at least the distal portion of the stopper 4300. Compression of the stopper 4300 as it enters the distal end section of the container 4221 may cause a reduction in size of the secondary fluid chamber 4350, thereby expelling secondary fluid from the secondary fluid chamber 4350.

In the embodiment illustrated in FIGS. 4A-4C, the plunger 4400 may be coupled to the stopper via a flanged plunger head 4410, which may be engaged by a shoulder portion 4330 of the plunger. However, the plunger 4400 may couple to the stopper by a press fit, screw connection, snap-fit, or other suitable connection mechanisms. The coupling may allow the plunger 4400 to move the stopper 4300 in both a distal and a proximal direction. In alternative embodiments, as described in further detail with reference to FIGS. 5A to 5C and FIG. 8, the plunger may engage the stopper without coupling thereto such that the stopper may be moved in a distal direction only and cannot be withdrawn.

A syringe 5000 according to another exemplary embodiment is shown in FIGS. 5A to 5D. The syringe 5000 is similar to the syringes 1000, 2000, 3000, 4000 of FIGS. 1A to 4C as discussed above. In FIGS. 5A to 5D, the stopper 5300 comprises a fully enclosed inner secondary fluid chamber 5350 defined by inner stopper wall 5310. In this exemplary embodiment, as the plunger 5400 applies force to move the stopper 5300 within the container 5200, a proximal region 5370 of the stopper 5300 may be compressed, increasing the pressure in the secondary fluid chamber 5350. The syringe 5000 further comprises a penetrating member 5500 within the container 5200 extending into the distal end section 5221 of the container 5200 from the distal end wall 5225.

Figure 5A:
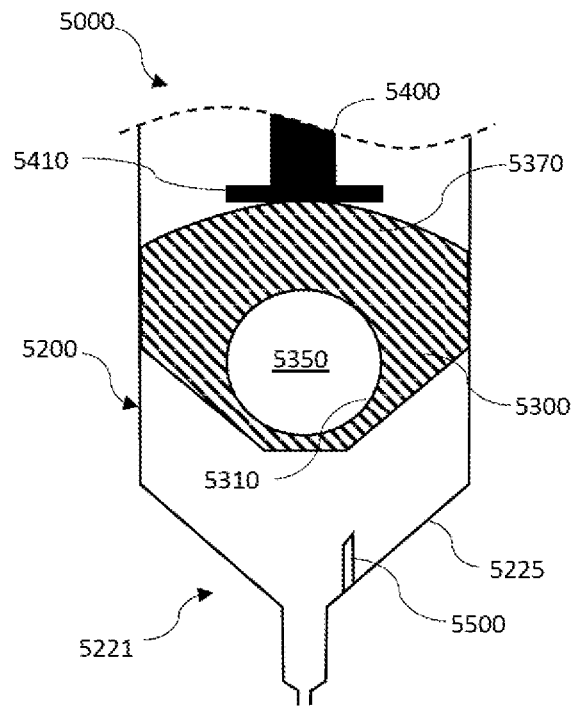
FIG. 5A is a partial cross-sectional view of a syringe according to at least one embodiment of the present disclosure.
Figure 5B:
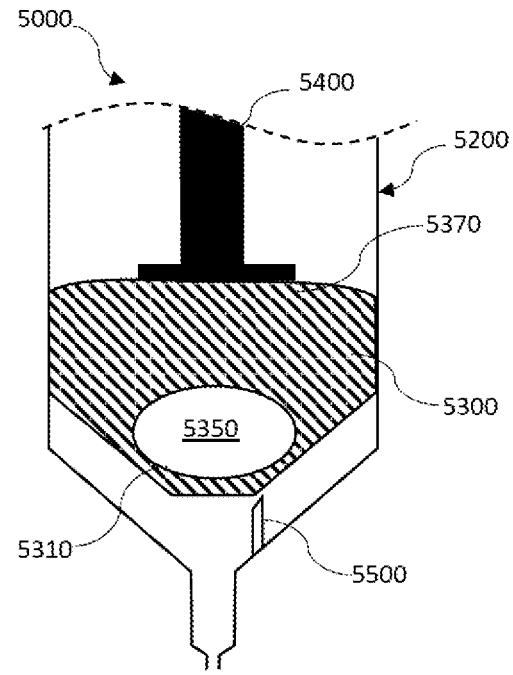
FIG. 5B is a partial cross-sectional view of the syringe of FIG. 5A with a stopper of the syringe moved to an intermediate position.
Figure 5C:
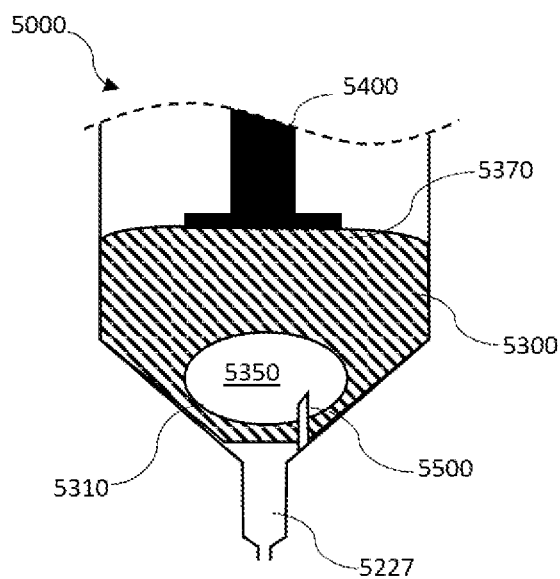
FIG. 5C is a partial cross-sectional view of the syringe of FIG. 5A with the stopper moved to an end position.
Figure 5D:
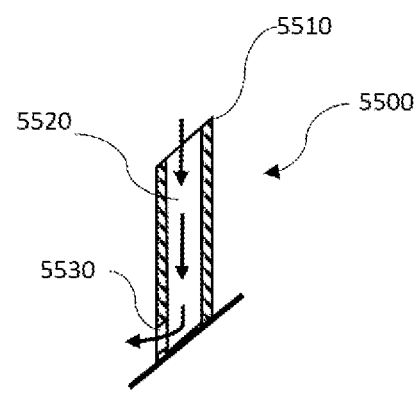
FIG. 5D is an enlarged view of a penetrating member of the syringe of FIG. 5A.

As shown in FIG. 5D, the penetrating member 5500 comprises a sharp proximal tip 5510 configured to pierce material of the stopper 5300. The penetrating member 5500 further comprises an internal lumen 5520 and a distal opening 5530 which together provide a fluid flow path 5520 for the secondary fluid to exit the secondary fluid chamber 5350.

In this exemplary embodiment, as the stopper 5300 approaches the distal stop position within the container 5200, the penetrating member 5500 pierces through the wall 5310 of the stopper 5300 and into the secondary fluid chamber 5350, releasing the pressurised secondary fluid through the lumen 5520 and opening 5530 and into the syringe tip chamber 5227.

In this and other embodiments, the plunger 5400 may engage the stopper 5300 without coupling thereto. For example, as shown in FIGS. 5A to 5C, a proximal surface of a head 5410 of the plunger 5400 may be configured to abut the stopper 5300 to engage the stopper 5300 without coupling thereto, to move the stopper in a distal direction within the container 5200. However, as the plunger 5400 does not couple to the stopper 5300, it cannot be used to withdraw the stopper 5300 in a proximal direction within the container 5200.

FIGS. 6A to 6C show an exemplary embodiment of a syringe 6000. In this exemplary embodiment, however, the stopper 6300 comprises a plurality of ribs 6380 on a distal facing surface of the stopper 6300. Secondary fluid chambers 6350, configured to contain secondary fluid, are defined between adjacent ribs 6380. In some embodiments, secondary fluid chambers may be defined between the ribs 6380 and an interior surface of the container 6200.

In the illustrated embodiment, as shown in FIG. 6C, the ribs extend in a radial direction, and may be radially spaced around a distal tip 6390 of the stopper 6300. The ribs extend towards, but stop short of the outer edge of the stopper 6300, such that the secondary fluid chambers 6350 may be joined adjacent to an outer rim of the stopper 6300 and at a central region of the stopper 6300. In other embodiments, however, the ribs 6380 may extend to an outer edge of the stopper 6300, such that the ribs 6380 abut the container 6200. Fluid flow paths 6320, allowing secondary fluid to exit the secondary fluid chambers 6350, may be provided by gaps between adjacent ribs 6380 adjacent to the distal tip 6390 of the stopper 6300.

The ribs 6380 may be deformable, such that, when the stopper 6300 reaches the distal stop position within the container 6200, the ribs 6380 may be compressed against the distal end wall 6225 of the container 6200, as shown in FIG. 6B. Compression of the ribs 6380 results in a compression of the secondary fluid contained in the secondary fluid chambers 6350, such that the secondary fluid may be expelled through the fluid flow paths 6320 and towards the distal end opening 6222 of the container 6200. Additionally or alternatively, the stopper 6300 may include a compressible porous material adjacent to the tip 6390 of the stopper.

The porous material may be a sponge material, for example, a hydrophobic sponge material.

In this and other embodiments, the fluid flow paths 6320 may be configured to direct secondary fluid into the syringe tip chamber 6227 at an angle, thereby to produce vortex flow. Vortex flow may enhance entrainment of the primary fluid residuum and promote ejection of the primary fluid residuum rather than mixing of the primary and secondary fluids.

Figure 7:
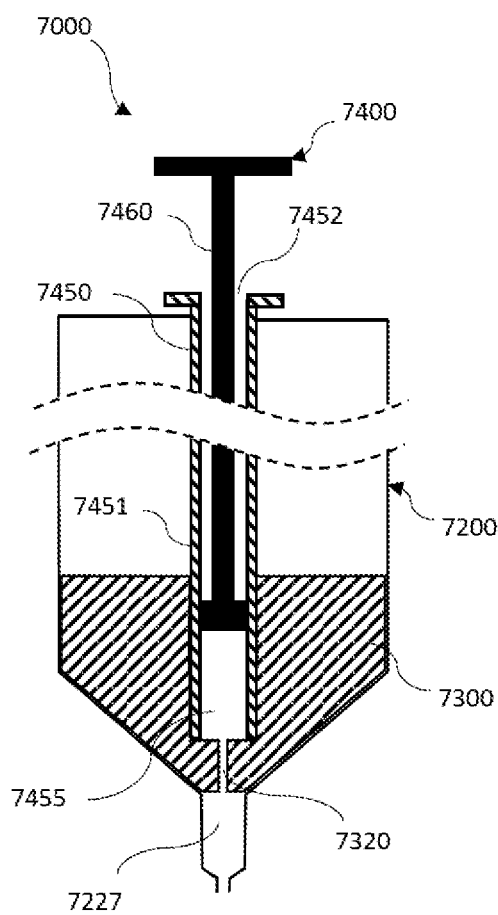
FIG. 7 is a cross-sectional view of a syringe according to at least one embodiment of the present disclosure.
Figure 8:
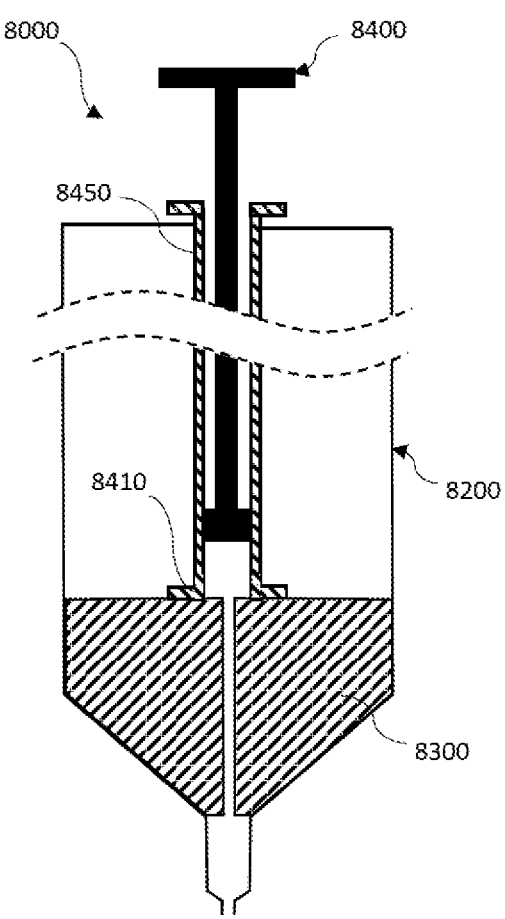
FIG. 8 is a cross-sectional view of a syringe according to at least one embodiment of the present disclosure.
Figure 9:
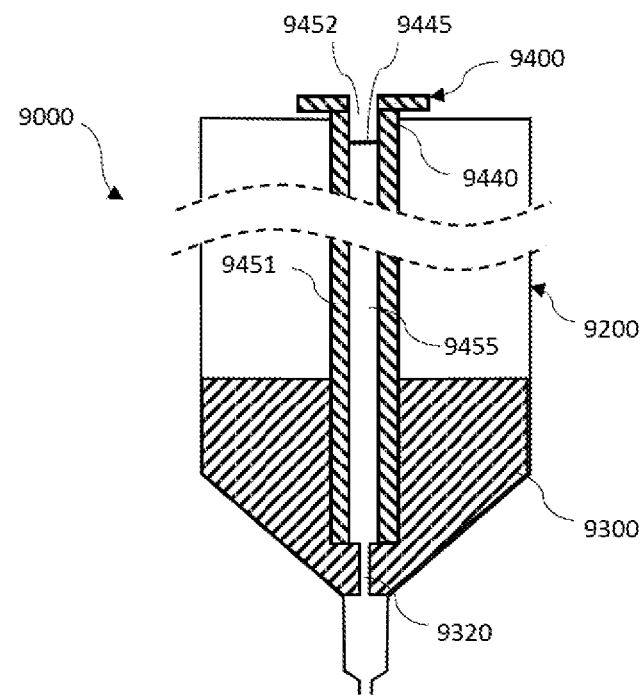
FIG. 9 is a cross-sectional view of a syringe according to at least one embodiment of the present disclosure.

Further embodiments of syringes 7000, 8000 and 9000 are shown in FIGS. 7 to 9, respectively. However, in each of these embodiments, as described in further detail below, the at least one secondary fluid chamber is comprised in a plunger of the syringe.

In the exemplary embodiment of FIG. 7, the syringe 7000 comprises a container 7200, stopper 7300, and plunger 7400. The plunger 7400 comprises a primary shaft 7450 and a secondary shaft 7460. The primary shaft 7450 has a side wall 7451 defining an interior lumen 7452. The secondary shaft 7460 may be axially slidably receivable in the interior lumen 7452 of the primary shaft 7450 and may be movable towards a distal end of the primary shaft 7450. The lumen 7455, together with a distal surface of the secondary shaft 7460, defines a secondary fluid chamber 7455 configured to contain a secondary fluid. The secondary fluid chamber 7455 is a variable volume chamber. That is, axial movement of the secondary shaft 7460 increases or reduces the size of the secondary fluid chamber 7455. Movement of the secondary shaft 7460 in a distal direction expels secondary fluid from the secondary fluid chamber 7455 through fluid flow path 7320 and into a syringe tip chamber 7227 of the container 7200.

The primary shaft 7450 may be engageable with the stopper 7300 and configured to apply force to move the stopper 7300 within the container 7200. In this exemplary embodiment, the primary shaft 7450 may be embedded within and coupled to the stopper 7300. However, in other embodiments, the plunger 7400 may engage the stopper 7300 by another mechanism. The force required to move the secondary shaft 7460 within the lumen 7452 may be configured to be greater than the force required to move the stopper 7300 within the container 7200 prior to reaching the distal stop position, such that force applied to the secondary shaft 7460 may be transmitted to the stopper 7300 via the primary shaft 7450 to move the stopper 7300 within the container 7200. Once the stopper 7300 reaches the distal stop position, further force may be applied to the secondary shaft 7460 to cause distal movement of the secondary shaft 7460 within the lumen 7452 of the primary shaft 7450. In some embodiments, the lumen 7452 may include a resisting member, such as a catch, a protrusion, or a narrowed portion, which inhibits movement of the secondary shaft 7460 beyond a predetermined point in the lumen 7452 before the stopper 7300 has reached the distal stop position.

FIG. 8 shows a syringe 8000 according to another exemplary embodiment. In FIG. 8 the primary plunger shaft 8450 may not be coupled to the stopper 8300. A proximal surface of a head 8410 of the plunger 8400 may be configured to abut the stopper 8300 to engage the stopper 8300 without coupling thereto, to move the stopper in a distal direction within the container 8200. However, as the plunger 8400 may not couple to the stopper 8300, it cannot be used to move the stopper 8300 in a proximal direction to withdraw the stopper 8300.

A syringe 9000 according to another exemplary embodiment is shown in FIG. 9. The syringe 9000 comprises a container 9200 configured to contain a primary fluid, a stopper 9300 and a plunger 9400. In this embodiment, the plunger 9400 comprises a side wall 9451 defining an internal lumen 9452. The lumen 9452 may be provided with a seal 9445 adjacent a proximal region 9440 of the plunger 9400, the seal and the lumen defining an internal secondary fluid chamber 9455 configured to contain a secondary fluid. The seal 9445 may be a frangible or penetrable membrane, a valve or other suitable sealing mechanisms. The proximal region 9440 comprises a fitting configured to receive a distal end of a secondary syringe to couple the secondary syringe in fluid communication with the lumen 9452. The seal 9445 may be configured to be pierced, penetrated, ruptured, dislodged, or otherwise opened when the secondary syringe is attached to the plunger 9400, thus fluidly connecting the secondary syringe to the secondary fluid chamber 9455. For example, the seal 9445 may be positioned within the lumen 9452 such that a distal tip of the secondary syringe penetrates the membrane upon connection to the plunger 9400. The secondary syringe may then be used to expel secondary fluid from the secondary fluid chamber 9455 through a fluid flow path 9320. For example, the secondary syringe may contain an additional volume of secondary fluid which may be injected into the secondary fluid chamber 9455 to drive secondary fluid through the fluid flow path 9320. In other embodiments, the secondary syringe may contain a tertiary fluid, which is different to both the primary and secondary fluids. In at least one embodiment, the tertiary fluid may be the same type of fluid as one or both of the primary and/or secondary fluids. In at least one embodiment, the primary, secondary and/or tertiary fluids may be provided at a different temperature to one or more of the other fluids.

Figure 10A:
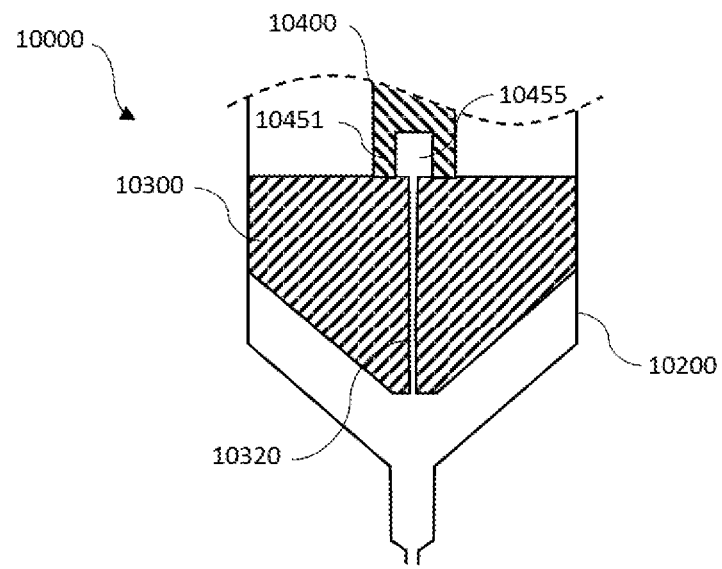
FIG. 10A is a partial cross-sectional view of a syringe according to at least one embodiment of the present disclosure.
Figure 10B:
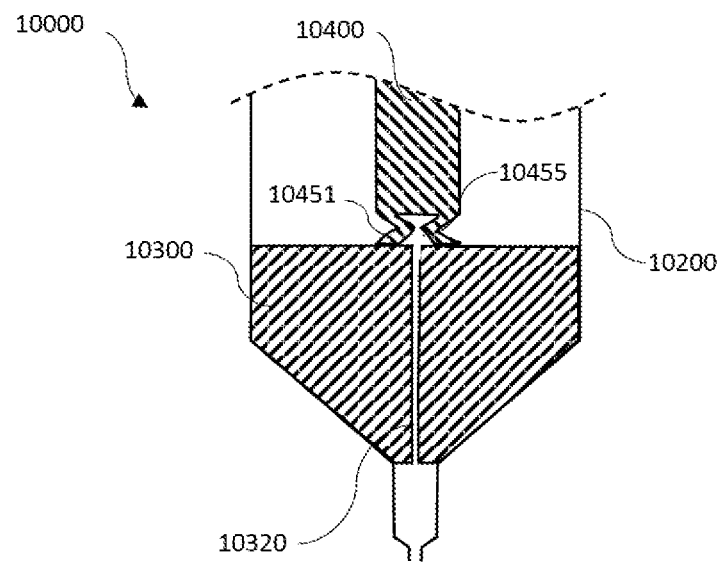
FIG. 10B is a partial cross-sectional view of the syringe of FIG. 10B with the stopper moved to an end position.

FIGS. 10A and 10B show a syringe 10000 according to another exemplary embodiment. The syringe 10000 comprises a container 10200 configured to contain a primary fluid, a stopper 10300 and a plunger 10400. In this embodiment, the plunger 10400 comprises a deformable side wall 10451 defining a secondary fluid chamber 10455 within the plunger 10400, the secondary fluid chamber 10455 configured to contain a secondary fluid. The stopper 10300 comprises a fluid flow path 10320 in fluid communication with the secondary fluid chamber 10455. When the stopper 10300 reaches a distal stop position within the container 10200 as shown in FIG. 10B, further force exerted on the plunger 10400 causes deformation (or collapse) of the side wall 10451, reducing the size of the secondary fluid chamber 10455 and driving secondary fluid through the fluid flow path 10320.

Figure 11A:
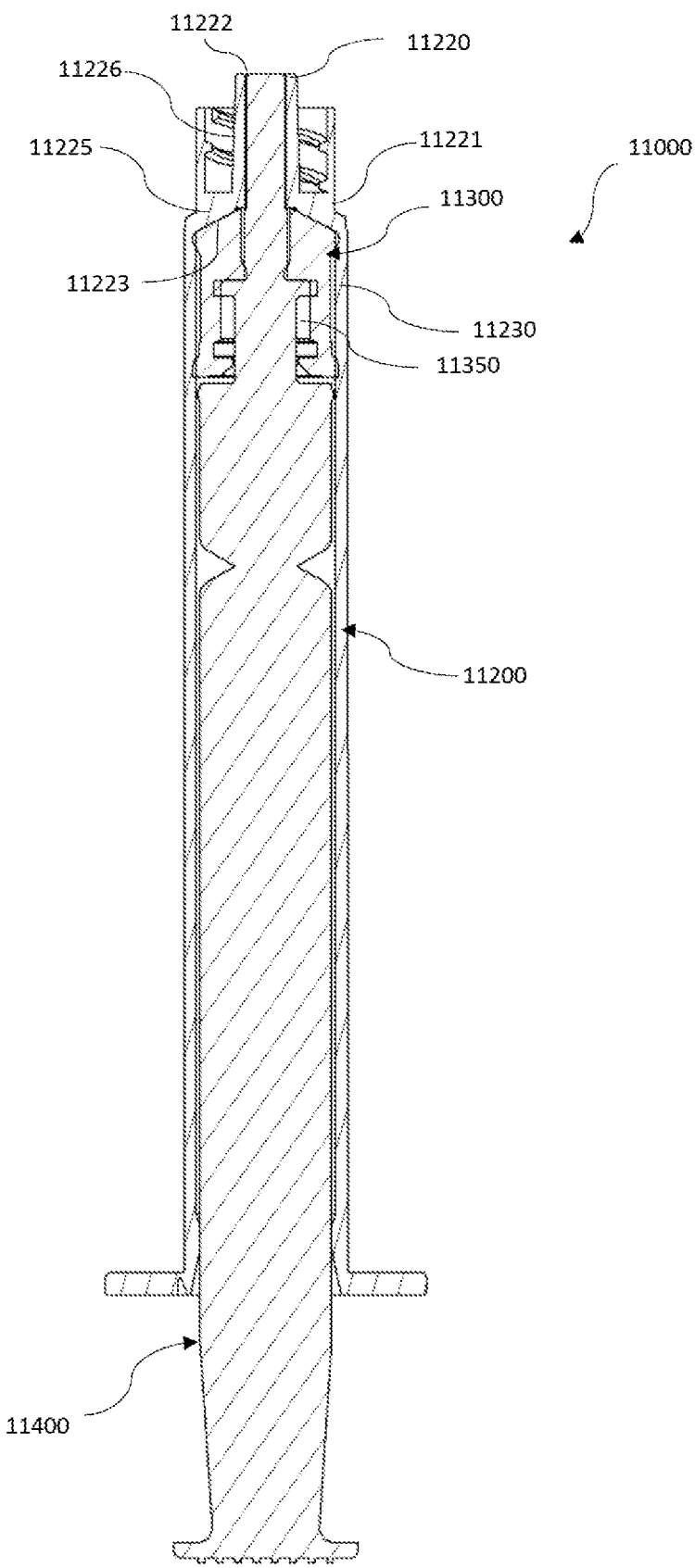
FIG. 11A is a cross-sectional view of a syringe according to at least one embodiment of the present disclosure.

A cross-sectional diagram of a syringe 11000 according to another exemplary embodiment is shown in FIG. 11A. The syringe comprises a container 11200 configured to contain a primary fluid, a stopper 11300 and a plunger 11400.

The container 11200 comprises a side wall 11230 extending in an axial direction of the container 11200 from a proximal end to a distal end 11220. A distal end section 11221 of the container 11200 includes an end wall 11225 extending radially inwards from the side wall 11230. In this exemplary embodiment, the distal end wall 11225 extends distally as well as radially inwardly, defining distal end section 11221 including a frusto-conical shape.

The distal end section 11221 further comprises a syringe tip 11226. The end wall 11225 has an outer edge connected to the side wall 11230 and an inner edge connected to the syringe tip 11226, the syringe tip 11226 projecting distally from the side wall 11230 and terminating in a distal end opening 11222. The syringe tip 11226 may be adapted for mounting of a needle hub thereon. In the exemplary embodiment, the syringe tip 11226 comprises a Luer connection element adapted for connection to a corresponding Luer needle connection. However, other needle connection types, such as a fixed needle connection, are also contemplated.

Figure 11B:
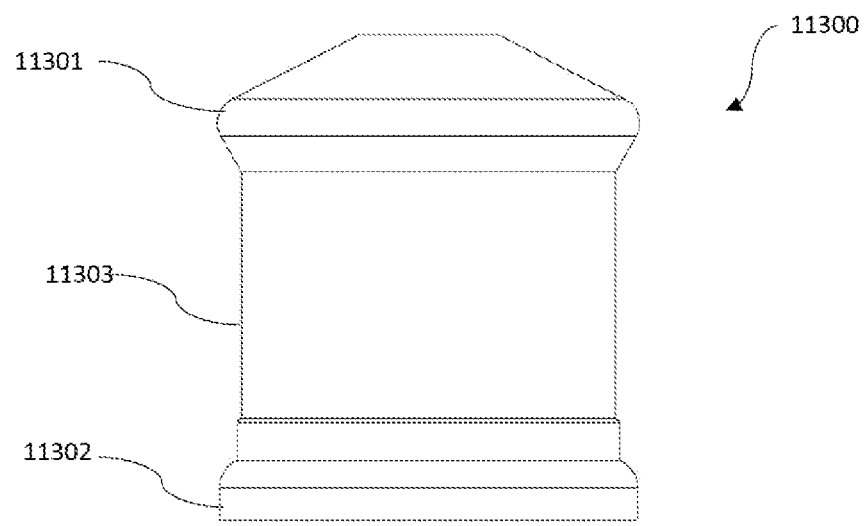
FIG. 11B is a front view of a stopper of the syringe of FIG. 11A.
Figure 11C:
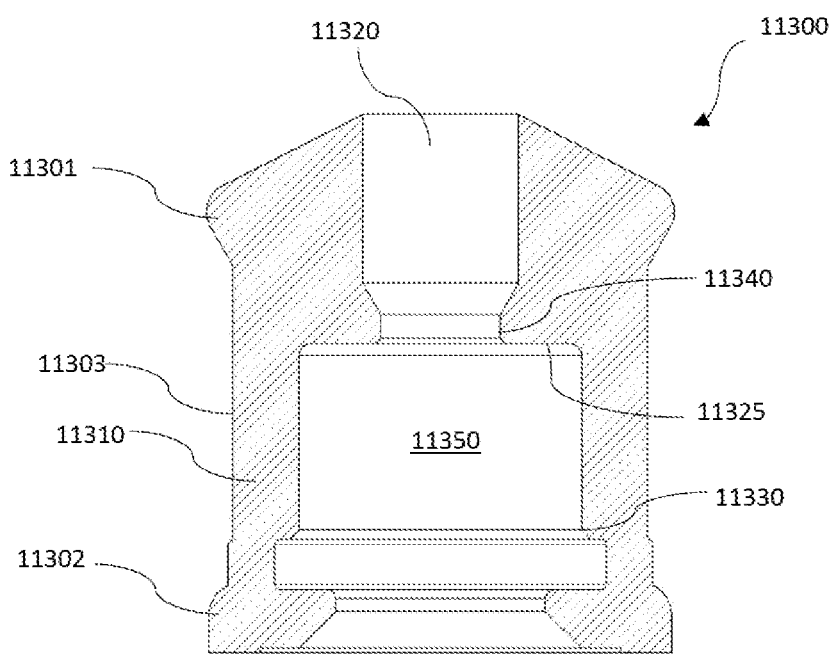
FIG. 11C is a cross-sectional view of the stopper of FIG. 11B.
Figure 11D:
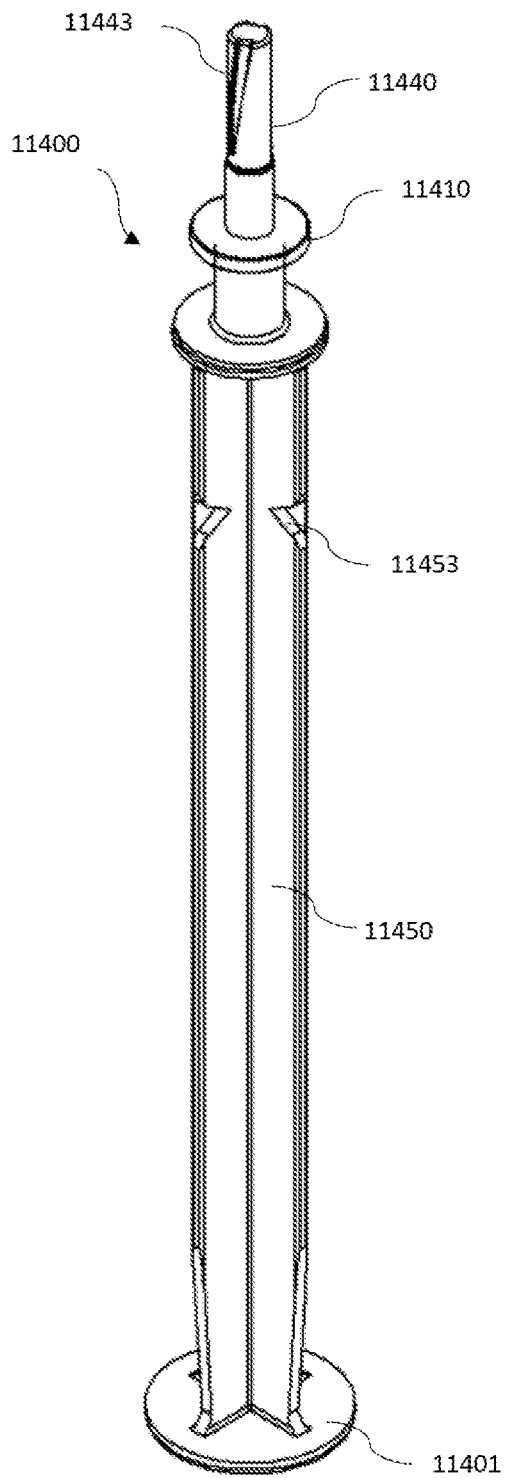
FIG. 11D is a perspective view of a plunger of the syringe of FIG. 11A.
Figure 11E:
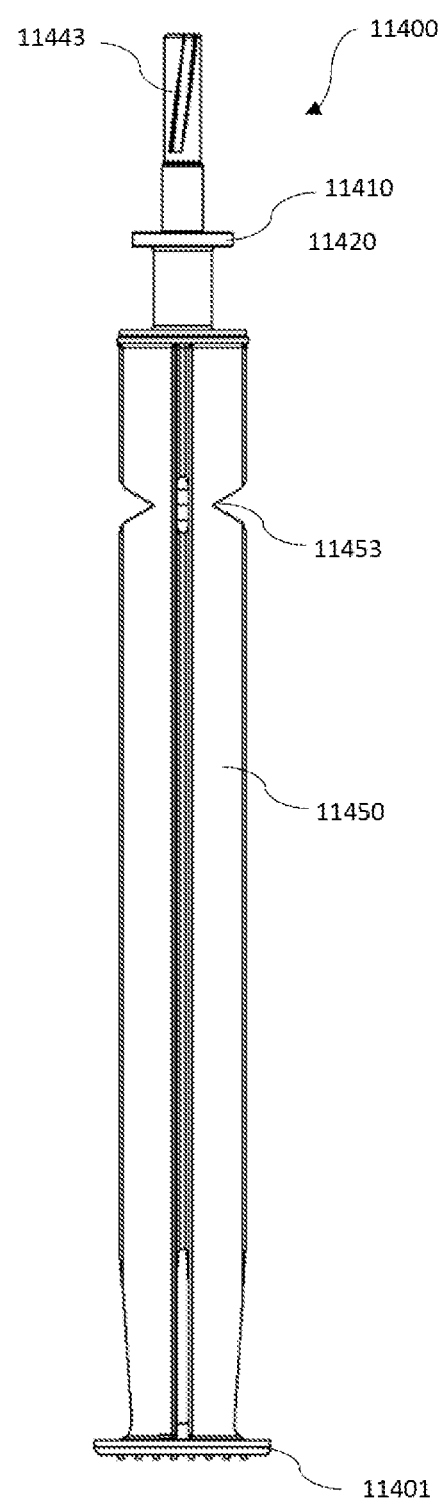
FIG. 11E is a front view of the plunger FIG. 11D.

The stopper 11300 is shown in greater detail in FIGS. 11B and 11C. The stopper 11300 is formed from a resiliently deformable material and is configured to be close-fittingly received within the container 11200 to form a fluid-tight engagement with an inner surface of side wall 11230. That is, at least a portion of the stopper 11300 may be configured to seal against an inner surface of the side wall 11230 to inhibit fluid from flowing between the stopper 11300 and the side wall 11230. In at least one embodiment, the stopper 11300 may include one or more ribs configured to provide the fluid-tight engagement. In the exemplary embodiment, the stopper 11300 includes a proximal circumferential rib 11301 and a distal circumferential rib 11302. The ribs 11301 and 11302 may be configured to compress against the inner surface of the side wall 11230 of the container 11200, such that fluid is inhibited from passing the ribs 11301, 11302. For example, as shown in FIG. 11J, the stopper 11300 may be configured to have an interference fit within the syringe container 11200, such that the ribs 11301, 11302 are compressed against the wall 11230 of the container 11200 to provide fluid-tight circumferential seals at the ribs 11301, 11302. The interference fit may be configured to be between about 0.3 mm to about 0.7 mm, between about 0.4 mm to about 0.6 mm, for example about 5 mm.

A distal region of the stopper 11300 is shaped to conform to the distal end wall 11225 of the container 11200. In the exemplary embodiment, the distal portion of the stopper 11300 has a frusto-conical shape corresponding to the frusto-conically shaped distal end section 11221 of the container 11200.

The stopper 11300 defines an inner, secondary fluid chamber 11350 configured to contain a secondary fluid. In the exemplary embodiment, the secondary fluid chamber 11350 is a cavity within the stopper 11300. The secondary fluid chamber 11350 may be defined by a wall 11310 of the stopper, which substantially surrounds the secondary fluid chamber 11350. The wall 11310 includes an inner end surface 11325 defining a distal end of the secondary fluid chamber 11350. A fluid flow path 11320 is provided by a bore extending distally from the inner chamber 11350 through a distal end of the stopper 11300 to allow secondary fluid to flow out of the inner chamber 11350, and the stopper 11300, towards the distal end opening 11222 of the syringe container 11200.

The plunger 11400 is configured to engage the stopper 11300 to apply a force to the stopper 11300 to move the stopper 111300 axially within the container 11200 towards the distal end 11220 to expel primary fluid through the distal end opening 11222. The plunger 11400 is shown in more detail in FIGS. 11D-F and includes a shaft 11450 having a finger grip 11401 at its proximal end. In at least one embodiment, the plunger shaft 11450 may include a weakened and/or frangible portion 11453. The weakened and/or frangible portion 11453 may comprise a portion of the plunger shaft 11450 having a reduced cross-sectional area, for example. This may provide a breakable area configured to enable snapping of the plunger shaft 11450 after use, to inhibit or prevent re-use of the syringe 11000.

Figure 11F:
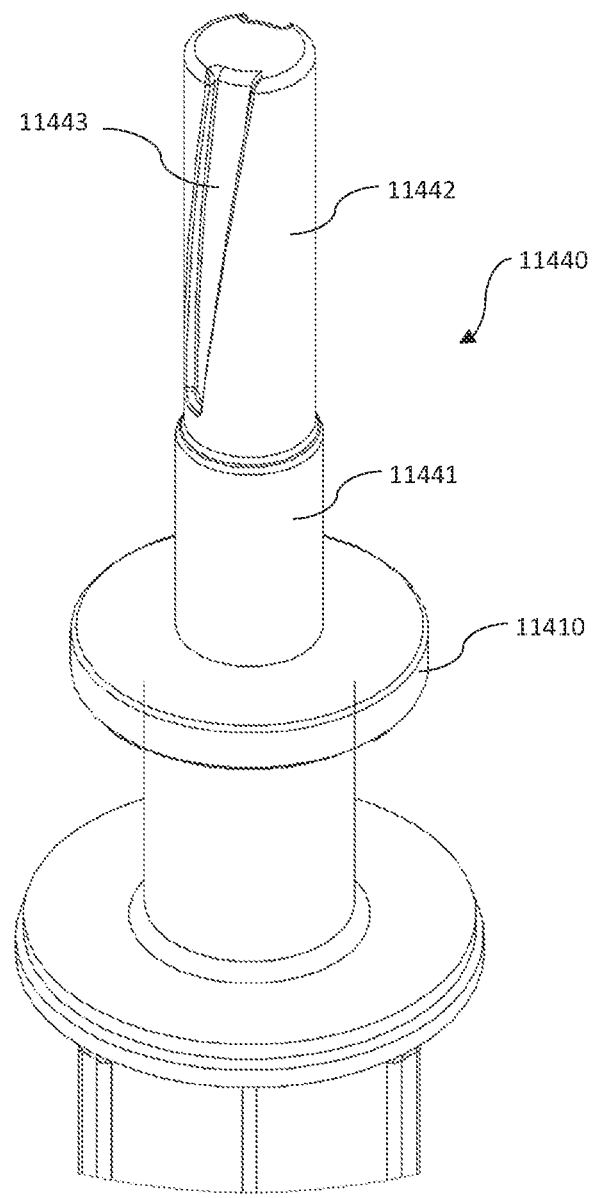
FIG. 11F is a partial perspective view of a distal end of the plunger of FIG. 11D.
Figure 11G:
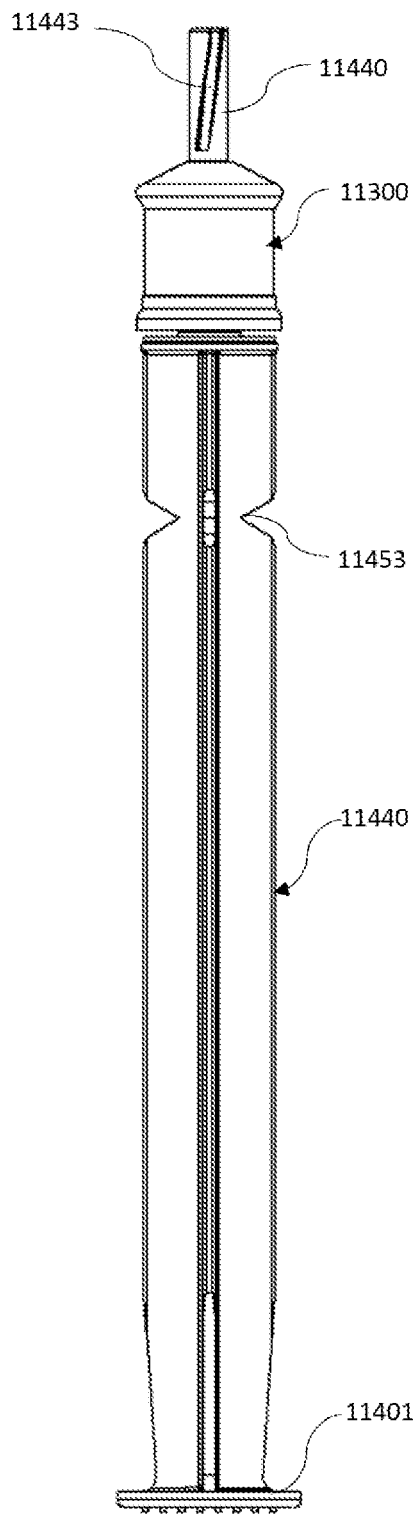
FIG. 11G is a front view of a plunger assembly including the stopper of FIG. 11B engaged with the plunger of FIG. 11D.
Figure 11H:
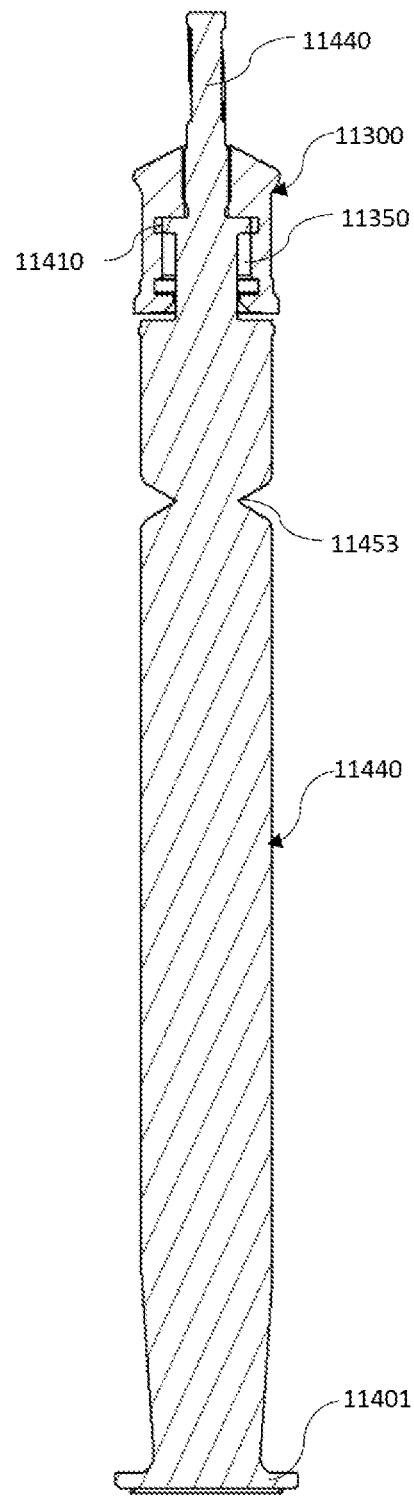
FIG. 11H is a cross-sectional view of the plunger assembly of FIG. 11A.
Figure 11J:
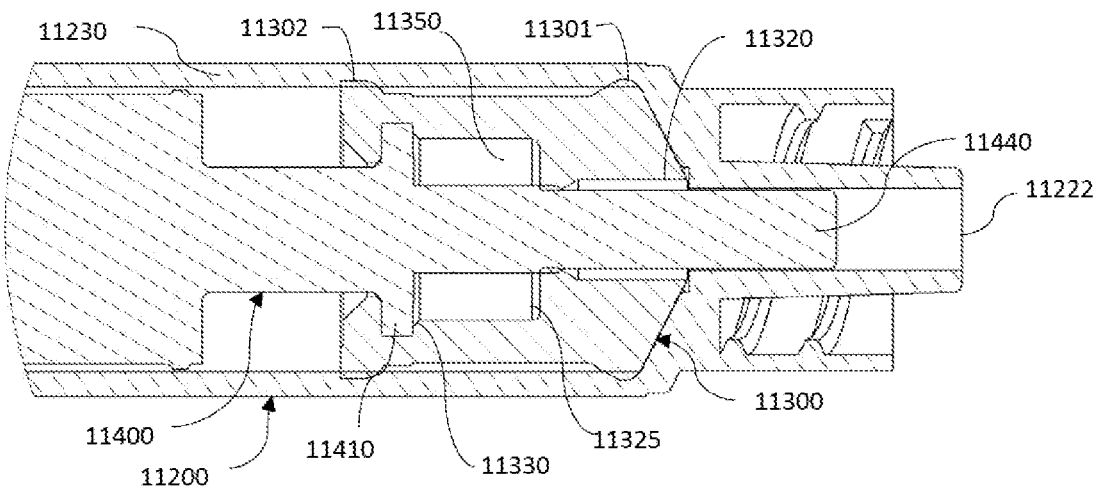
FIG. 11J is a partial cross-sectional view of the syringe of FIG. 11A, with the plunger in a first engagement position.
Figure 11K:
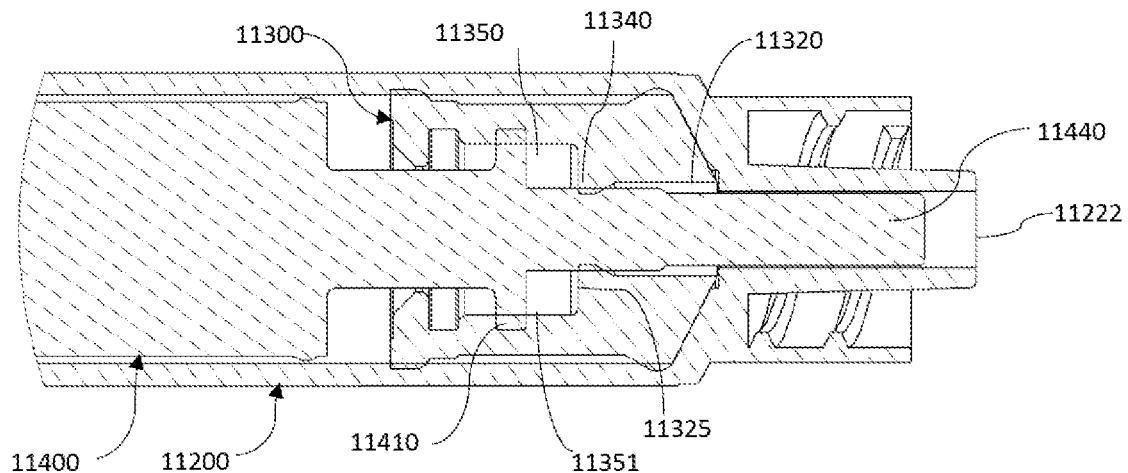
FIG. 11K is a partial cross-sectional view the syringe of FIG. 11A, with the plunger transitioning between a first engagement position and a second engagement position.
Figure 11L:
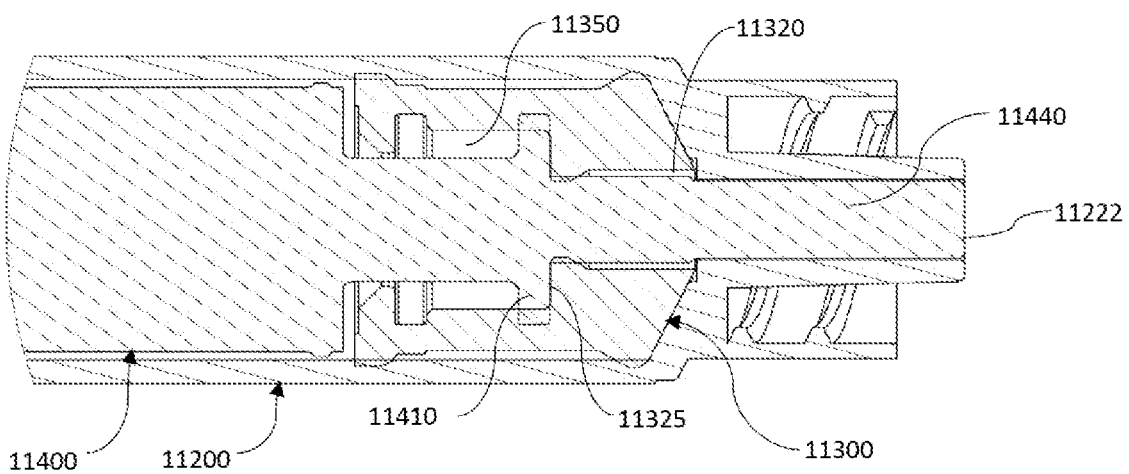
FIG. 11L is a partial cross-sectional view of the syringe of FIG. 11A, with the plunger in a second engagement position.

The plunger 11400 may be movably engageable with the stopper 11300 between a first engagement position as shown in FIG. 11J and a second engagement position as shown in FIG. 11L. FIG. 11K shows the plunger 11400 transitioning between the first and second engagement positions. When the plunger 11400 is in the first engagement position, a flange 11410 of the plunger engages a radially inwardly extending shoulder protrusion 11330 of the stopper 11300 which resists movement of the plunger 11400 from the first engagement position to the second engagement position. In the first engagement position, force applied to the plunger 11400 moves the stopper 11300 towards the distal end 11220 of the container 11200 to expel primary fluid from the distal end opening 11222.

The plunger 11400 advances the stopper 11300 axially within the container 11200 in a distal direction, expelling primary fluid through the distal end opening 11222, until the stopper 11300 reaches a distal stop position within the container 11200 in which the stopper 11300 abuts the inner distal end surface 11223, which is a proximally facing surface of the distal end wall 11225 of the container 11200 as shown in FIG. 11A. When the stopper 11300 reaches the distal stop position, a residual volume (residuum) of primary fluid may remain in the syringe, such as in the tip chamber 11227 and/or in an attached needle cannula, distal of the stopper 11300.

The force applied via the plunger 11400 to move the stopper 11300 within the container 11200 may be configured to be less than a force applied to the plunger 11400 to move the plunger 11400 from the first engagement position to the second engagement position, by overcoming resistance of the shoulder protrusion 11330, for example. The plunger 11400 may thus be prevented from moving from the first engagement position to the second engagement position until completion of the action that moves the stopper 11300 to the distal stop position.

Once the stopper 11300 reaches the distal stop position, increased force may be applied to the plunger 11400 to overcome the resistance of the shoulder protrusion 11330, such that the plunger 11400 advances from the first engagement position to the second engagement position. In the exemplary embodiment, the shoulder protrusion 11330 of the stopper 11300 may be resiliently deformable. The flange 11410 of the plunger may be configured to have a greater rigidity than the shoulder protrusion 11330.

FIG. 11K shows the plunger having overcome the resistance of the shoulder protrusion 11300 such that the flange 11410 enters the secondary fluid chamber 11350. As the plunger 11400 moves between the first engagement position and the second engagement position, the flange 11410 of the plunger 11400 moves through the inner chamber 11350 of the stopper 11300, driving secondary fluid through the fluid flow path 11320. When in the second engagement position, as shown in FIG. 11L, the flange 11410 abuts inner end surface 11325 of the wall 11310 of the stopper 11300. In this embodiment, once in the second engagement position, the plunger 11400 is inhibited from moving distally any further with respect to the stopper 11300.

The flange 11410 may be configured to have an interference fit within the secondary fluid chamber 11350. This may be seen, for example, in FIG. 11K. An outer rim of the flange 11410 may form a seal with an inner surface 11351 of the inner chamber 11350 of the stopper. Movement of the flange 11410 in the distal direction may therefore displace, or drive, secondary fluid from the inner chamber 11350. The displaced secondary fluid may be expelled through the fluid flow path 11320, towards the distal end opening 11222 of the syringe tip 11226.

As the flange 11410 moves through the secondary fluid chamber 11350 from the first engagement position to the second engagement position, the wall 11310 of the stopper may flex, and/or bulge, radially outwards. The stopper wall 11310 may be configured to be flexible to accommodate this movement. Further, the stopper 11300 may include a narrowed waist portion 11303 between ribs 11301, 11302, providing a clearance between the stopper 11300 and the wall 11230 of the syringe container 11200 when the plunger is in the first engagement position or the second engagement position. That is, the stopper 11300 may have a reduced outer diameter in the region of the secondary fluid chamber 11350, providing clearance between an outer surface of the stopper 11300 and an inner surface of the wall 11230 of the syringe container. The clearance may allow for outwards flexing of the wall 11310 of the stopper 11300 as the plunger flange 11410 moves between the first engagement position and the second engagement position. In at least one embodiment, the clearance between the stopper 11300 and the container 11200 at the waist portion 11303 may be configured such that the waist portion 11303 of the stopper 11300 does not contact the syringe container 11200 during the outwards flexing. In at least one embodiment, the clearance may be configured to minimise a contact pressure of the waist portion 11303 contacting the syringe container 11200 during the outwards flexing.

A ratio R of the clearance between the stopper 11300 and the container 11200 at the waist portion, to the thickness of the wall 11310 at the waist portion may be configured to provide a desired degree of flexibility. For example, the ratio may be calculated as follows:

Container inner diameter=$C$

Stopper waist portion outer diameter=$W$

Stopper wall thickness at waist portion=$T$

Clearance $(Z)=(C-W)/2$ $R=T/Z$.

The ratio may be configured based on an interference between the ribs 11301, 11302 and the wall 11230 of the syringe. In at least one embodiment, for an interference of about 0.5 mm, the ratio R may be configured to be about 4+/−about 10%, for example between about 3.5 and about 4.5, between about 3.6 and about 4.4, between about 3.7 and about 4.3, between about 3.8 and about 4.2, between about 3.9 and about 4.1, or about 4.

Exemplary dimensions for a 3 ml syringe and a 5 ml syringe are provided in Table 1, below.

TABLE 1

|  | 3 ml syringe | 5 ml syringe |
| --- | --- | --- |
| Stopper waist portion outer diameter, W | 8.4 | 11.7 |
| Container inner diameter, C | 9.1 | 12.35 |
| Stopper wall thickness at waist portion, T | 1.3 | 1.325 |
| Clearance, Z | (9.1 − 8.4)/2 = 0.35 | (12.35 − 11.7)/2 = 0.325 |
| Ratio, R | 1.3/0.35 = 3.71 | 1.325/0.325 = 4.08 |

Figure 12A:
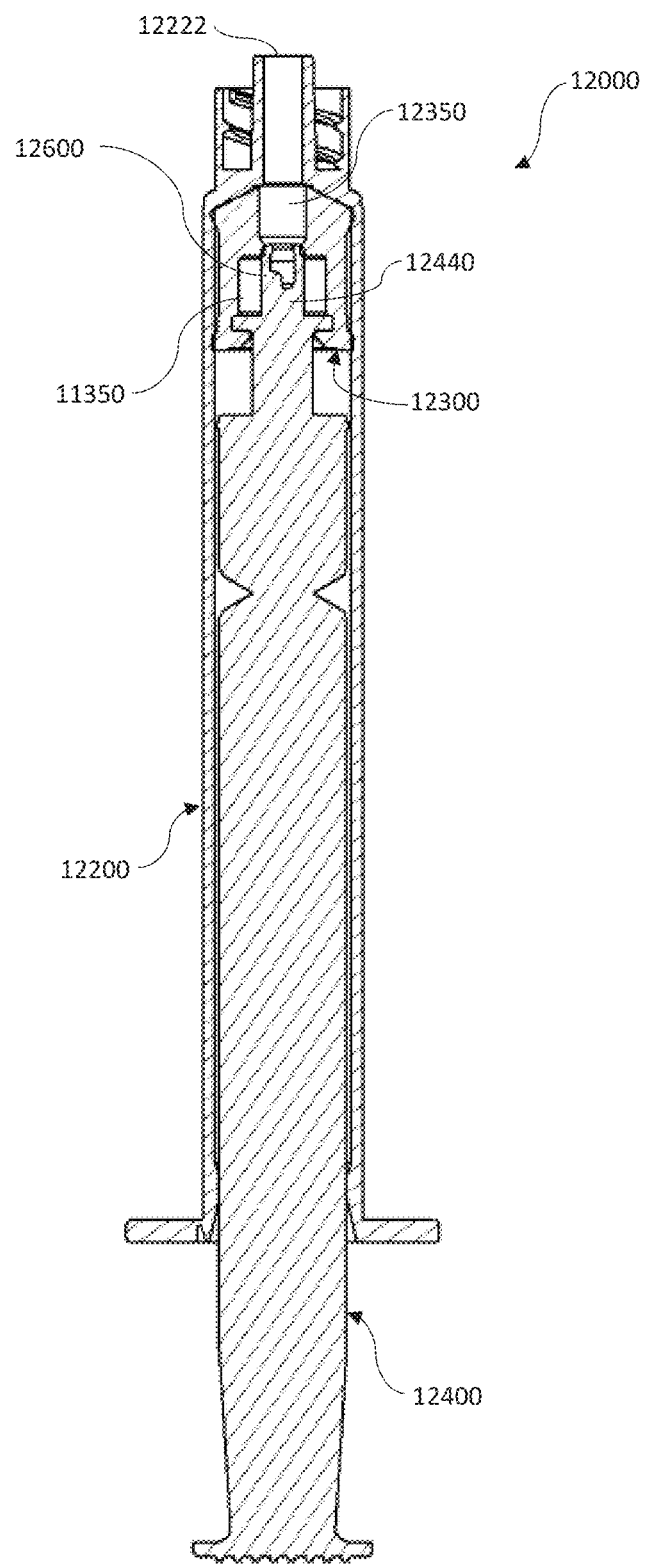
FIG. 12A is a cross-sectional front view of a syringe according to at least one embodiment of the present disclosure.

In at least one embodiment, the plunger 11400 includes a nib 11440, as shown in detail in FIG. 11F. The nib 11440 may include a proximal portion 11441 and a distal portion 11442. When the plunger 11400 is assembled in the syringe container 11200 and with the stopper 11300 in a first engagement position, the nib 11440 extends distally of the stopper 11300, through the fluid flow opening 11320 and may extend into the syringe tip 11226. Alternatively, in at least one other embodiment, the nib 11440 may be shortened and may not extend into the syringe tip 11226. One example of a shortened nib is shown in FIG. 12A, for example. A shortened nib may also be used for syringe containers having a fixed needle connection, or other needle connection type, rather than a Luer style connection as illustrated.

The secondary fluid may be expelled through the syringe tip 11226 around the nib 11440 of the plunger 11400. A fluid flow path may be defined between an outer surface of the nib 11440 and an inner wall of the syringe tip 11226, to allow for secondary fluid to pass therethrough. In at least one embodiment, the nib 11440 includes one or more channels 11443 in its outer surface to guide the secondary fluid as it is expelled. As shown in FIG. 11F, the channels may extend along the nib 11440 in a longitudinal direction to a distal end of the nib 11440. The channels may follow a curved path. In the exemplary embodiment, two opposing channels 11443 having opposing helical profiles are defined on opposite sides of the nib 11440.

The channels 11443 may extend along a portion of the nib 11440. For example, as shown in FIG. 11F, the channels may extend along the distal portion 11442 of the nib 11440, while the proximal portion 11441 of the nib 11440 may be free from channels and may have a smooth surface.

The channels 11443 may serve to guide the secondary fluid around the nib 11440, aiding in evacuation of primary fluid from the syringe tip 11226. In experiments, it was found that, in the absence of the channels, small droplets of primary fluid remained clinging to the inner walls of the syringe tip 11226. Inclusion of one or more channels 11443 in the surface of the nib 11440 resulted in a more complete evacuation of primary fluid from the syringe 11200. In particular, it was found that a pair of opposed channels having helical profiles provided the greatest effect in reducing the primary fluid remaining in the syringe tip. Features of the channels 11443 may also be configured for ease of manufacture of the plunger 11400, by injection moulding for example.

In at least one embodiment, the stopper may comprise a sealing flange 11340 for forming a fluid-tight seal around the plunger 11440, for example, around the proximal portion 11441 of the nib 11440. That is, the sealing flange 11340 may inhibit fluid from passing between the sealing flange 11340 and an outer surface of the nib 11440. The sealing flange 11340 may provide a secondary fluid-tight seal, that is, in addition to the fluid-tight seal provided between the plunger flange 11410 and the wall 11310 of the secondary fluid chamber 11350. As may be seen in FIG. 11K the interference fits between the plunger 11400 and the stopper 11300 at the plunger flange 11410 and sealing flange 11340 seal the secondary fluid chamber 11350 at its ends.

Secondary fluid may be expelled from the secondary fluid chamber 11350 under a pressure sufficient to overcome the fluid-tight seal between the sealing flange 11340 and the nib 11440, thus allowing secondary fluid to pass therethrough from the secondary fluid chamber 11350 into the fluid flow path 11320. The seal between the plunger flange 11410 and the inner wall 11351 may be configured to be stronger than the seal between the sealing flange 11340 and the nib 11440, such that pressure sufficient to overcome the fluid-tight seal between the sealing flange 11340 and the nib 11440 does not overcome the fluid-tight seal between the plunger flange 11410 and the wall 11351 of the stopper 13100. This may inhibit secondary fluid from being expelled from the secondary fluid chamber 11350 in a proximal direction, away from the fluid flow opening 11222.

In at least one embodiment, a syringe may include a needle engagement mechanism, configured to engage a retractable needle. The syringe may be configured such that the needle may be withdrawn into the syringe container after use. This may reduce the likelihood of injury from the needle. The needle engagement mechanism may be configured to engage a proximal portion of the retractable needle after injection such that sliding action of the plunger assembly in the proximal direction, pulling the plunger out of the syringe container, retracts the needle within the syringe container. In at least one embodiment, the needle engagement mechanism is configured to cause tilting of the needle, once retracted into the syringe barrel.

Exemplary retractable needle engagement mechanisms, which provide for tilting of the needle upon retraction, are described in further detail in documents WO 2004/014470 A1 and WO 2018/001624 A1.

In some embodiments, the needle engagement mechanism may be comprised in the stopper. In at least one embodiment described herein, the needle engagement mechanism is comprised in the plunger.

Figure 12D:
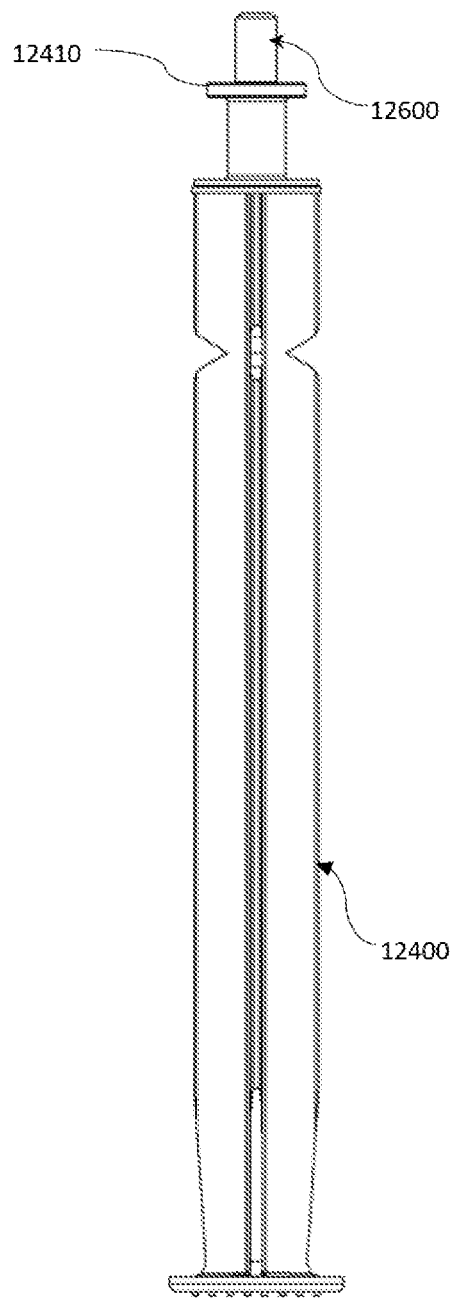
FIG. 12D is a side view of the plunger of FIG. 12A.
Figure 12E:
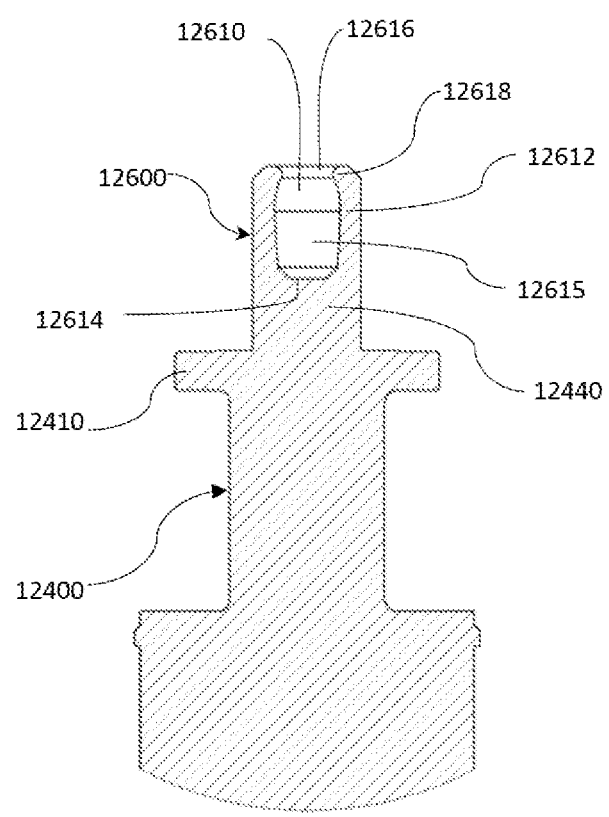
FIG. 12E is a partial cross-sectional side view of the plunger of FIG. 12D.

FIG. 12A shows a syringe 12000, according to an exemplary embodiment. The syringe 12000 includes a container 12200, a stopper 12300 and a plunger 12400. The container 12200 and stopper 12300 may include one or more feature of the container 11200 and stopper 11300 of the syringe 11000 as described with reference to FIGS. 11A to 11L. The plunger 12400 is shown in more detail in FIGS. 12D and 12E, and may include a needle engagement mechanism 12600 in the nib 12440. The needle engagement mechanism 12600 may be configured to engage a proximal end of a needle assembly, such as a casing attached to a needle cannula. In alternative embodiments, a needle engagement mechanism may be provided in the stopper.

FIGS. 12B and 12C show the plunger 12400 engaged with the stopper 12300 to form a plunger assembly. As with syringe 11000, a fluid-tight seal is provided between the plunger flange 12410 and the stopper 12300. In this embodiment, the nib 12400 is shorter than the nib 11400 of the syringe 11000 described with reference to FIGS. 11A to 11L and does not extend distally of the stopper 12300. However, the length of nib 12440 may be longer than a length of the secondary fluid chamber 12350, such that sealing flange 12340 forms a fluid-tight seal with the nib 12440 when the plunger 12400 is in the first engagement position, as can be seen in FIG. 12C. The length of the nib 12400 may be configured such that, in the first engagement position, the needle engagement mechanism 12600 does not or cannot engage the retractable needle. This may reduce the likelihood of accidental activation of the needle engagement mechanism 12600.

In this exemplary embodiment, the needle engagement mechanism 12600 includes a cavity 12610 in the nib 12440, the cavity being configured to receive a proximal portion of a retractable needle. The needle engagement mechanism 12600 is shown in more detail in FIG. 12E. The cavity 12610 may be defined by one or more walls 12612 of the nib 12440 of the plunger 12400 extending distally from a base 12614 of the nib 12440 of the plunger. A distal end of the one or more walls 12612 of the nib 12440 may define a mouth 12616 of the cavity 12610. A catch portion 12618 may be provided at a distal end of the nib 12440. In the exemplary embodiment, the catch portion 12618 is a circumferential flange extending radially inwardly from the one or more walls 12612 of the nib at or adjacent the mouth 12616. The catch portion 12612 may be configured to engage a portion of a retractable needle, e.g. a proximal portion of the retractable needle when the proximal portion is received in the cavity 12610.

In at least one embodiment, the syringe 12000 may be configured to tilt at least a needle cannula of a retractable needle upon retraction of the needle cannula, via the distal end opening of the syringe container 12200, into the syringe container 12200. Tilting of the needle cannula may inhibit the needle cannula from being pushed forwards again through the distal end opening of the syringe container 12200. This may reduce the likelihood of needle stick injuries. In at least one embodiment, the needle engagement mechanism includes a dissymmetric portion configured to apply force to tilt the needle cannula. The dissymmetric portion may be dissymmetric about a longitudinal axis, for example. In alternative embodiments, the dissymmetric portion may be dissymmetric in relation to a horizontal plane. In the exemplary embodiment, the base 12614 of the cavity 12610 includes a ramped surface or lug 12615 configured to apply a tilting force a retractable needle cannula when a proximal region of the retractable needle cannula is engaged in the cavity 12610. This is described in further detail below, with reference to FIGS. 13B-E. In at least one embodiment, the lug 12615 of the present needle retraction mechanism 12600 may comprise one or more features as described, for example, in document WO 2004014470 A1 in relation to the internal ramp (88) of retractor (50).

In alternative embodiments, the catch portion 12618 may be configured to apply a tilting force to the retractable needle cannula. For example, the catch portion 12618 may be dissymmetric about a longitudinal axis. Alternatively, the catch portion 12618 may include surfaces for contacting the retractable needle which are offset in a horizontal plane, for example. In at least one embodiment, the catch portion 12618 may include dissymmetrical bearing surfaces having one or more features as described, for example, in document WO 2018001624 A1 in relation to first and second bearing zones (22) and (23), for example. In at least one alternative embodiment, a portion of a retractable needle assembly may be configured to cause tilting of the needle cannula upon retraction into the syringe container 12200.

Figure 12F:
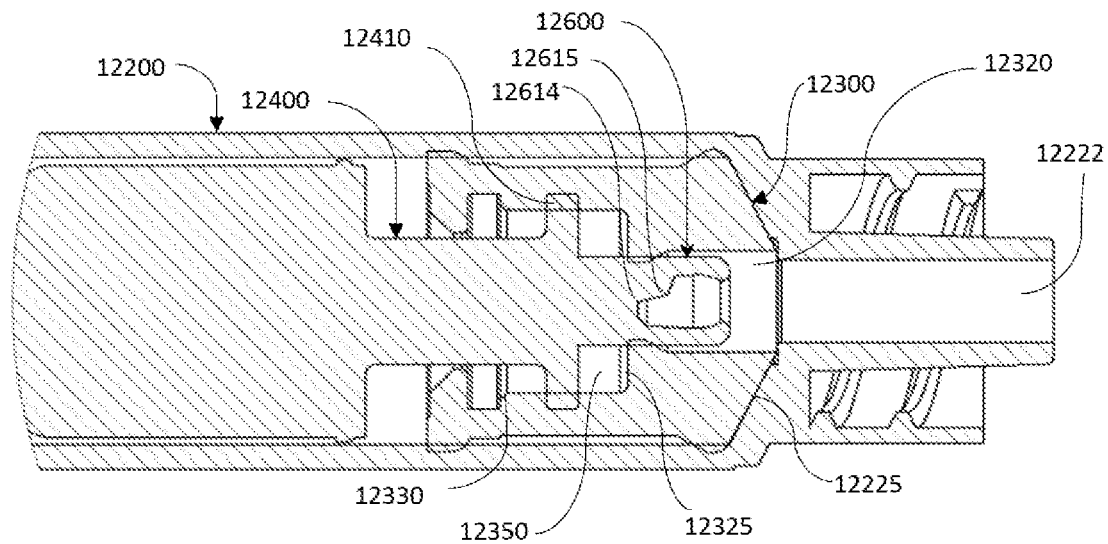
FIG. 12F is a partial cross-sectional front view of the syringe of FIG. 12A with the plunger shown transitioning between a first engagement position and a second engagement position.
Figure 12G:
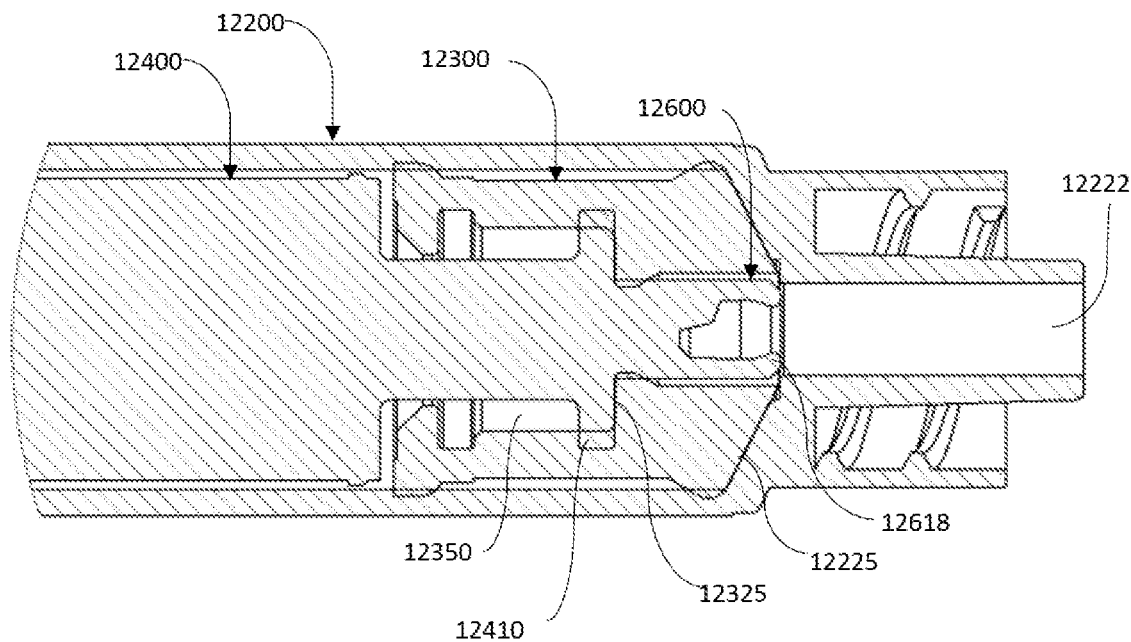
FIG. 12G is a partial cross-sectional front view of the syringe of FIG. 12A with the plunger shown in a second engagement position.

FIG. 12F shows the plunger 12400 transitioning between the first engagement position and the second engagement position. In the exemplary embodiment, when the plunger 12400 is in the second engagement position as shown in FIG. 12G, the needle engagement mechanism 12600 is positioned in the fluid flow path 12320 with its distal end aligned with a distal end of the stopper 12300.

Additionally, in at least one embodiment, the syringe container and/or the plunger may include stops (not shown) for preventing the plunger from being removed from the syringe container. The stops may be configured to allow the plunger assembly to be withdrawn far enough to achieve retraction and tilting of the needle, and/or to expose the frangible portion 12453 of the plunger shaft for snapping, but may inhibit separation of the plunger assembly from the syringe container. This may minimise the possibility of re-use of the syringe. Preventing re-use of the needle, syringe container and/or plunger assembly may be desirable to avoid transmission of infectious materials, for example.

Figure 13A:
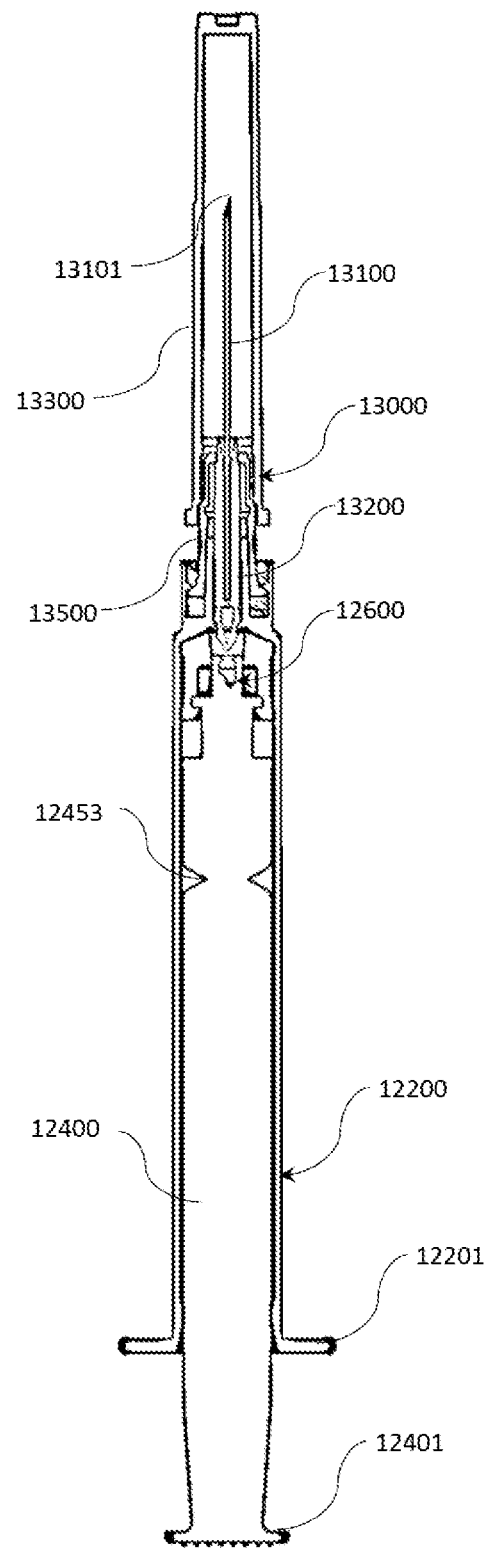
FIG. 13A is cross-sectional front view of the syringe of FIG. 12A engaged with a retractable needle assembly.

FIG. 13A shows the syringe 12000 engaged with a needle assembly 13000. The needle assembly 13000 may include a needle cannula 13100 and a casing 13200 engaged with a proximal end of the needle cannula. An interface 13500 is configured for mounting the needle assembly 13000 to the syringe container 12200, for example by a threaded connection with a Luer connection element of the syringe container 12200. The needle assembly 13000 is provided with a shield 13300 for shielding at least a distal end of the needle cannula 13100. When mounted on the syringe 12000, the hollow interior of the needle cannula 13100 may be in fluid communication distal end opening 12222 of the syringe container 12200 such that fluid may be expelled through the distal end opening 12222 and through the syringe cannula 13100. In at least one embodiment, the needle assembly 13000 may be a retractable needle assembly.

As shown in FIG. 13A, when the plunger 12400 is in the first engagement position with the stopper 12300, the needle engagement mechanism is spaced from a distal end of the stopper 12300. As such, when the stopper 12300 reaches the distal stop position within the container 12200 the needle engagement mechanism 12600 does not engage the retractable needle casing 13200.

Figure 13B:
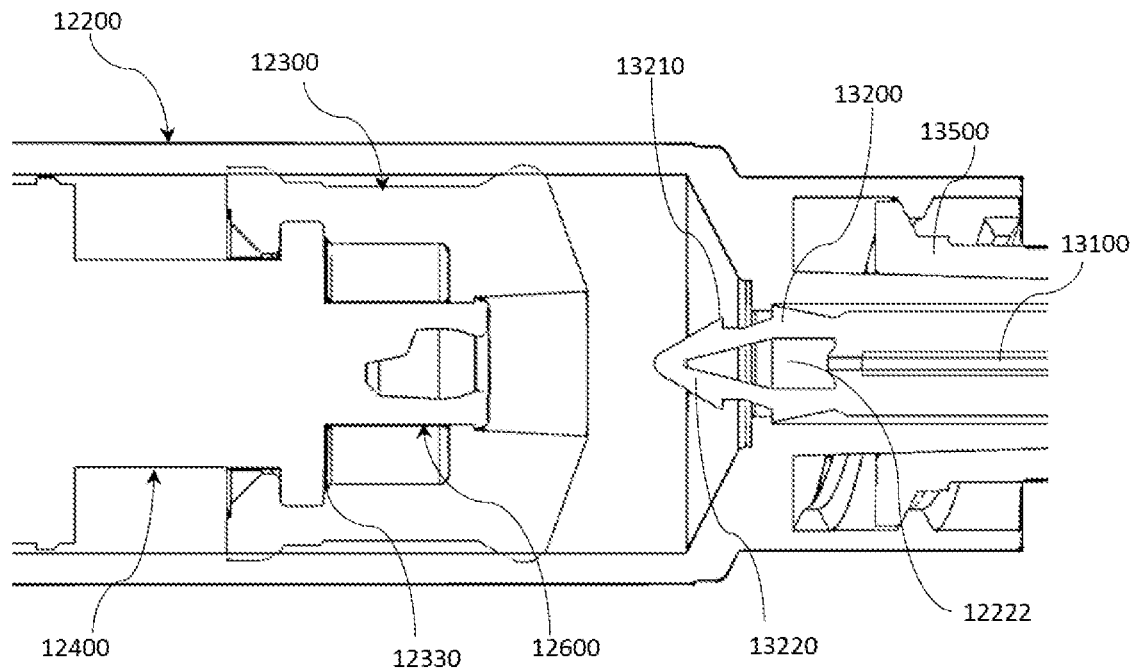
FIG. 13B is a partial cross-sectional front view of the syringe and needle assembly of FIG. 13A.

FIGS. 13B to 13E show a sequence of steps in an injection process using syringe 12000. In use, syringe 12000 may be presented to the user as shown in FIG. 13B, with the plunger 12400 engaged with the stopper 12300 in a first engagement position and spaced rearwardly from the distal stop position, that is, spaced rearwardly from the inner distal end surface of the syringe container 12200.

The needle shield may be removed. The user may apply a force to move the plunger 12400 within the container 12200. For example, the user may apply force between a finger grip 12401 of the plunger 12400 and a finger flange 12201 of the syringe container 12200 to move the plunger assembly within the syringe container 12200.

Figure 13C:
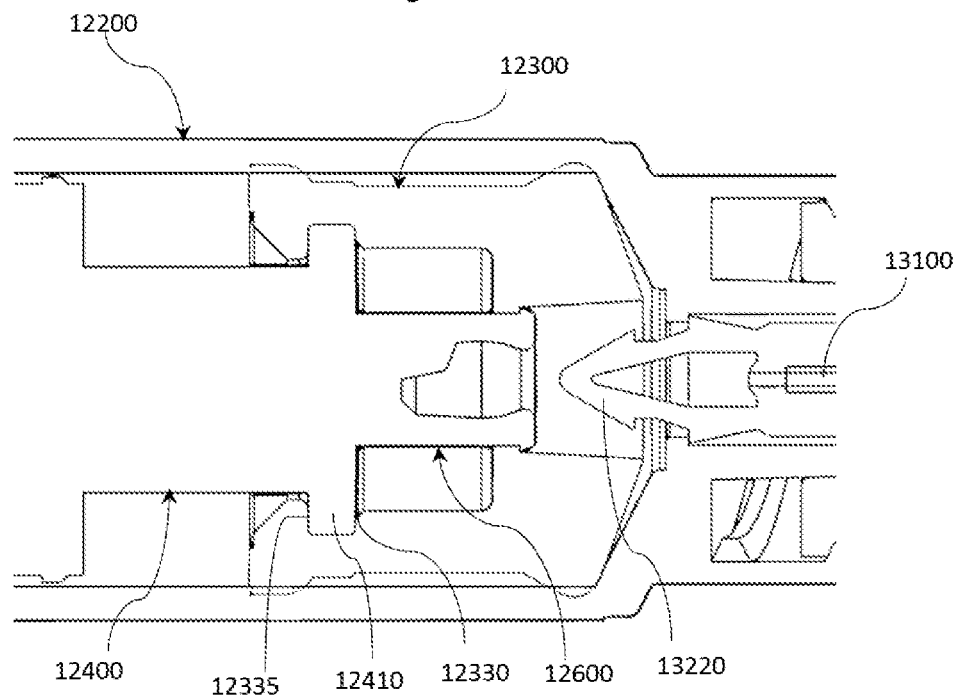
FIG. 13C is a partial cross-sectional front view of the syringe and needle assembly of FIG. 13A, with the plunger shown in transition between a first engagement position and a second engagement position.

In at least one embodiment, the user may initially draw primary fluid into the syringe container 12200. The user may first move the plunger and stopper into the distal stop position, as shown in FIG. 13C, to expel air present in the syringe container 12200. In the first engagement position, the plunger 12400 is inhibited from travelling distally relative to the stopper 12300 by the resistance between a shoulder protrusion 12330 of the stopper 12300 and a flange 12410 of the plunger 12400. The length of the nib 12440 may be configured such that the needle engagement mechanism 12600 does not engage the retractable needle 13000 when the stopper 12300 is at the distal stop position and the plunger 12400 is in the first engagement position. This may reduce the likelihood of inadvertent engagement and retraction of the needle cannula 13100 prior to performing an injection procedure, which may render the syringe 12000 inoperable.

The user may then draw fluid (for example, the primary fluid) into the syringe container 12200, for example by applying a withdrawing force to the plunger 12400 to move the plunger 12400 in proximal direction within the syringe container 12200. The plunger 12400 is inhibited from travelling proximally relative to the stopper 12300 by abutment between the flange 12410 of the plunger 12400 and a rear wall 12335 of the stopper 12300. As such, application of the withdrawing force to the plunger 12400 moves the stopper 12300 in a proximal direction within the container 12000, creating a reduced pressure in the syringe container 12200 distal of the stopper 12300. In alternative embodiments, the syringe 12000 may be provided to the user pre-filled.

A user may operate the syringe 12000 to expel primary fluid, for example in an injection procedure, by applying force to the plunger 12400 to move the stopper 12300 within the container 12000 towards the distal end opening 12222.

Figure 13D:
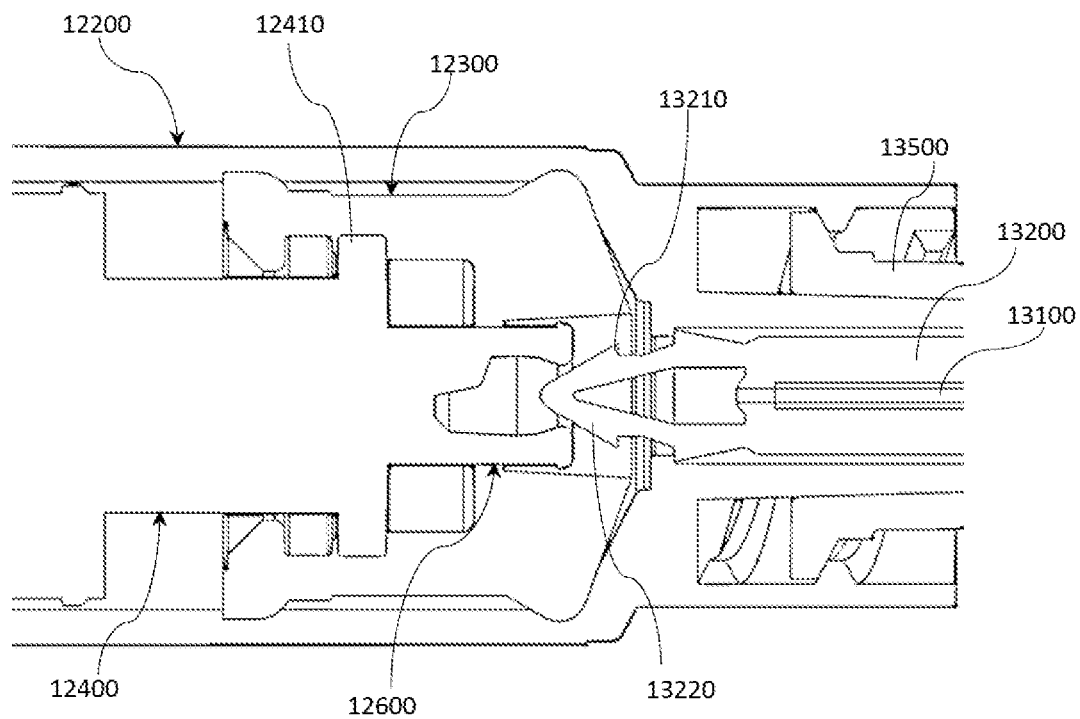
FIG. 13D is a partial cross-sectional front view of the syringe and needle assembly of FIG. 13A, with the plunger shown in transition between a first engagement position and a second engagement position.

Once the stopper 12300 reaches the distal stop position within the syringe container 12200, as shown in FIG. 13C, increased force may be applied to the plunger 12400 to overcome the resistance of the stopper shoulder protrusion 12330 and cause the plunger 12400 to move between the first engagement position and the second engagement position (for example, as shown in FIG. 11K, 12F, or 13D). As the plunger 12400 moves relative to the stopper 12300, the plunger flange 12410 moves through the secondary fluid cavity 12350, expelling secondary fluid from the secondary fluid chamber 12350 towards the distal end opening 12222. The secondary fluid may be expelled through the needle cannula 13100 of the attached needle assembly 13000, to expel at least a portion of a residual volume of primary fluid from the syringe 12000 and the needle cannula 13100.

Figure 13E:
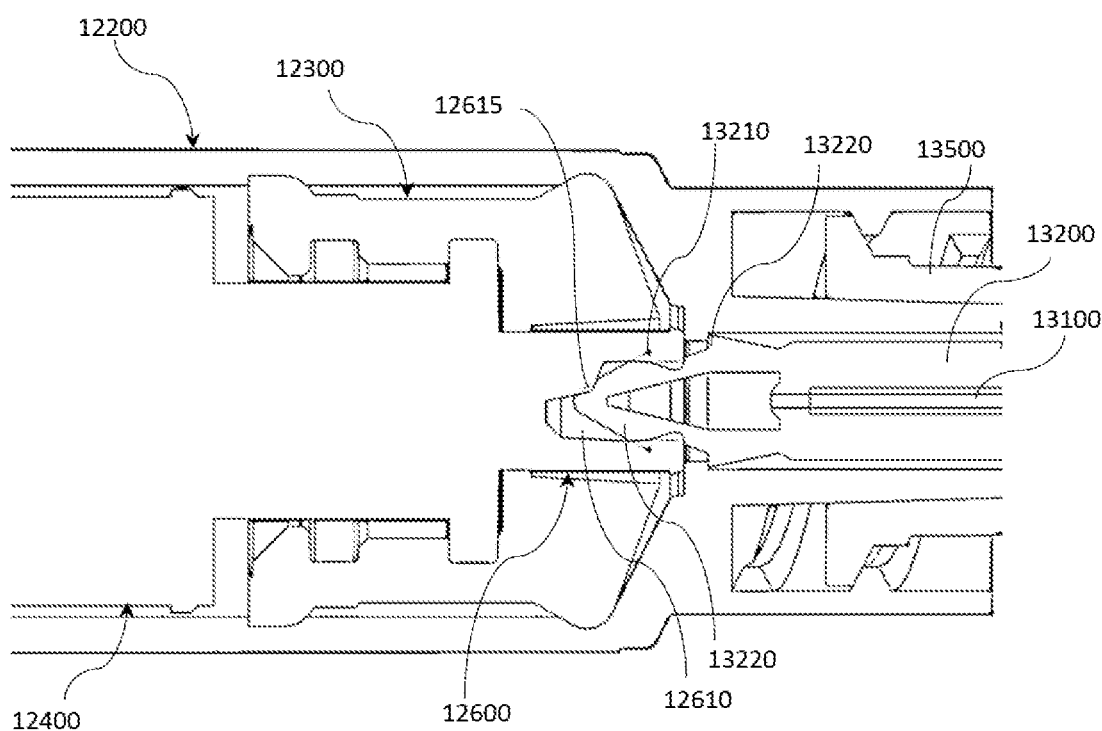
FIG. 13E is a partial cross-sectional front view of the syringe and needle assembly of FIG. 13A, with the stopper shown in a distal stop position and the plunger shown in a second engagement position engaging the retractable needle.

As the plunger 12400 transitions to the second engagement position (or upon the plunger 12400 reaching the second engagement position) the needle engagement mechanism 12600 may engage a proximal region of the needle casing 13200. In the exemplary embodiment, the catch portion 12618 of the needle engagement mechanism 12600 is configured to cooperate with engagement portion 13220 at a proximal end of the needle casing 13200. FIG. 13E shows the engagement portion 13220 docked in the cavity 12610 of the needle engagement mechanism 12600. In this configuration, the catch portion 12618 engages the stops 13210 of the needle casing 13200 to retain engagement portion 13220 within the cavity 12610. Engagement of the needle engagement mechanism 12600 of the plunger 12400 with the engagement portion 13220 of the needle casing 13200 may also cause disengagement of at least a portion of the retractable needle assembly 13000 from the syringe container 12200 to enable retraction of at least the needle cannula 13100 within the syringe container 12200. The plunger 12400 may then be pulled in a proximal direction until a distal tip 13101 of the retractable needle cannula 13100 is withdrawn into the syringe container 12200.

Figure 13F:
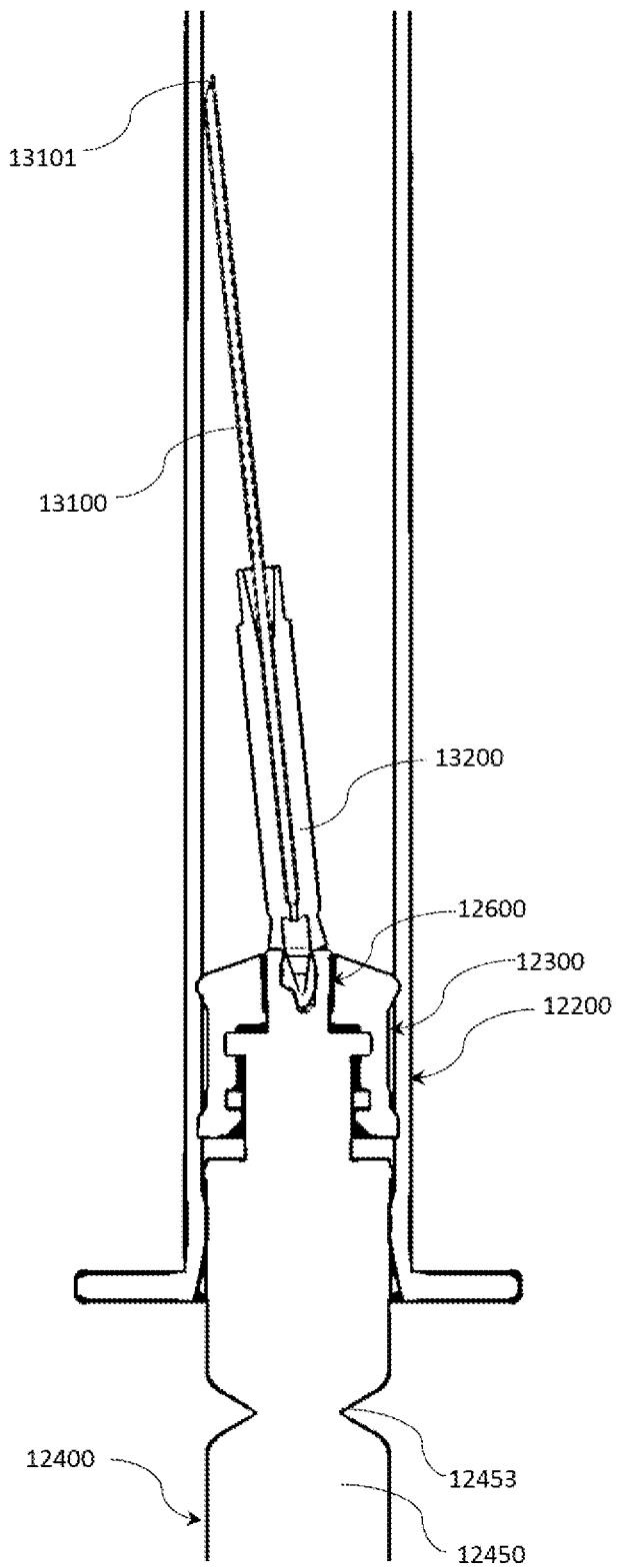
FIG. 13F is a partial cross-sectional front view of the syringe and needle assembly of FIG. 13A, showing the needle cannula retracted into the syringe container.

As shown in FIG. 13F, once retracted into the syringe container 12200, the needle cannula 13100 may be caused to tilt, for example by the lug 12615 of the cavity 12610, inhibiting subsequent re-use of the needle 13000. The lug 12615 of the needle engagement mechanism 12600 applies a force to the engagement portion 13220 of the casing 13200 of the needle assembly 13000, such that the needle cannula 13100 tilts relative to the longitudinal axis of the syringe 12000 upon retraction into the container 12200

Movement of the plunger 12400 in the proximal direction to retract the needle cannula 13100 of the retractable needle assembly 13000 may expose the frangible portion 12453 of the shaft 12450 of the plunger 12400 beyond a proximal end of the syringe container 12200, as may be seen in FIG. 13F. A user may then snap the plunger shaft 12450 at the frangible portion 12453, further inhibiting re-use of the syringe 12000.

Syringes according to the present disclosure may be used to deliver medicament to a subject by injection, for example. In at least one such embodiments, the primary fluid may be a liquid medicament for delivery to the subject the secondary fluid may be a gas or liquid (such as saline).

In at least one embodiment, the secondary fluid may provide a second component of the medicament. Syringes according to the present disclosure may facilitate combination of medicament components during the injection process. For example, in at least one embodiment, the secondary fluid may provide a degrading ligand for the medicament allowing slower release. Such a ligand may degrade the medicament if combined prior to injection. As such, the syringe provides for controlled timing of the combination of the primary and secondary fluids.

Ejection of the gas or liquid from the at least one secondary fluid chamber may more reliably effect evacuation of the medicament from the syringe than conventional syringes.

In some embodiments, the syringe may be configured to inject a volume of the secondary fluid after injection of the primary fluid is completed. Injection of the secondary fluid may provide evidence of injection. For example, the secondary fluid may comprise a marker fluid, providing visual, sonic or electronic indication of the injection having been performed. For example, the secondary fluid may contain a dye or tracer element providing evidence of medicament delivery. In other embodiments, the secondary fluid may have antiseptic and/or antibiotic properties.

Further advantages of the claimed subject matter will become apparent from the following examples describing certain embodiments of the claimed subject matter.

1A. A syringe comprising:
 a container for containing a primary fluid, the container comprising a proximal end and a distal end and having a distal end opening at the distal end;
 a stopper movably arranged within the container, and
 a plunger engageable with the stopper and configured to apply a force to the stopper to move the stopper within the container;
 wherein the syringe comprises at least one secondary fluid chamber configured to contain a secondary fluid;
 wherein the plunger is configured to move the stopper towards the distal end of the container, to expel primary fluid from the container through the distal end opening; and
 wherein the plunger is configured to expel secondary fluid from the at least one secondary fluid chamber towards the distal end opening, to expel at least a portion of a residual volume of primary fluid through the distal end opening.

1B. A syringe comprising:
 a container for containing a primary fluid, the container comprising a proximal end and a distal end and having a distal end opening at the distal end;
 a stopper movably arranged within the container, and
 a plunger engageable with the stopper and configured to apply a force to the stopper to move the stopper within the container;
 wherein the syringe comprises at least one secondary fluid chamber configured to contain a secondary fluid;
 wherein the plunger is configured to move the stopper towards the distal end of the container, to expel primary fluid from the container through the distal end opening; and
 wherein the plunger is configured to expel secondary fluid from the at least one secondary fluid chamber towards the distal end opening, to expel at least a portion of a residual volume of primary fluid through the distal end opening,
 wherein the plunger is movably engageable with the stopper between a first engagement position and a second engagement position, wherein, when the plunger is in the first engagement position, the plunger is configured to move the stopper towards the distal end of the container to expel primary fluid from the distal end opening and wherein, when the plunger moves from the first engagement position to the second engagement position, secondary fluid is expelled from the at least one secondary fluid chamber through the fluid flow path and towards the distal end opening 1C. A syringe comprising:
 a container for containing a primary fluid, the container comprising a proximal end and a distal end and having a distal end opening at the distal end;
 a stopper movably arranged within the container, and
 a plunger engageable with the stopper and configured to apply a force to the stopper to move the stopper within the container;
 wherein the syringe comprises at least one secondary fluid chamber configured to contain a secondary fluid;
 wherein the plunger is configured to move the stopper towards the distal end of the container, to expel primary fluid from the container through the distal end opening; and
 wherein the plunger is configured to expel secondary fluid from the at least one secondary fluid chamber towards the distal end opening, to expel at least a portion of a residual volume of primary fluid through the distal end opening,
 wherein the plunger is movably engageable with the stopper between a first engagement position and a second engagement position, wherein, when the plunger is in the first engagement position, the plunger is configured to move the stopper towards the distal end of the container to expel primary fluid from the distal end opening and
 wherein, when the plunger moves from the first engagement position to the second engagement position, secondary fluid is expelled from the at least one secondary fluid chamber through the fluid flow path and towards the distal end opening,
 wherein the stopper comprises at least one fluid flow path for secondary fluid to exit the at least one secondary fluid chamber
 wherein the stopper comprises one or more walls which define the at least one secondary fluid chamber,
 wherein the at least one secondary fluid chamber comprises an inner chamber in the stopper.

2A. The syringe of example 1A, wherein the stopper comprises at least one fluid flow path for secondary fluid to exit the at least one secondary fluid chamber.

3A. The syringe of example 2A wherein the stopper comprises one or more walls which define the at least one secondary fluid chamber.

4A. The syringe of example 3A wherein the at least one secondary fluid chamber comprises an inner chamber in the stopper.

5A. The syringe of example 3A wherein the at least one secondary fluid chamber is defined between an inner surface of a wall of the container and an outer surface of the stopper.

6A. The syringe of example 5A wherein an outer wall of the stopper comprises at least one recessed surface, wherein the at least one secondary fluid chamber is defined between the at least one recessed surface and the interior surface of the wall of the container.

7A. The syringe of any one of examples 3A to 6A, wherein the plunger is movably engageable with the stopper between a first engagement position and a second engagement position, wherein, when the plunger is in the first engagement position, the plunger is configured to move the stopper towards the distal end of the container to expel primary fluid from the distal end opening and wherein, when the plunger moves from the first engagement position to the second engagement position, secondary fluid is expelled from the at least one secondary fluid chamber through the fluid flow path and towards the distal end opening.

8A. The syringe of example 7A, wherein, when the plunger moves from the first engagement position to the second engagement position, at least a portion of the plunger enters into a chamber in the stopper.

9A. The syringe of example 8A, wherein the chamber that the plunger enters into is the at least one secondary fluid chamber.

10A. The syringe of example 9A, wherein, when plunger moves from the first engagement position to the second engagement position, the at least a portion of the plunger that enters into the at least one secondary fluid chamber directly displaces secondary fluid in the at least one secondary fluid chamber so that the displaced secondary fluid is expelled through the fluid flow path and towards the distal end opening.

11A. The syringe of example 8A, wherein the plunger enters into a rod receiving chamber that is different from the at least one secondary fluid chamber.

12A. The syringe of example 11A, wherein, when the plunger moves from the first engagement position to the second engagement position, the at least a portion of the plunger that enters into the rod receiving chamber causes displacement of one or more of the stopper walls, such that the at least one secondary fluid chamber is reduced in size and secondary fluid is expelled from the at least one secondary fluid chamber through the fluid flow path and towards the distal end opening.

13A. The syringe of example 7A, wherein, when the plunger moves from the first engagement position to the second engagement position, the plunger causes displacement of one or more of the stopper walls, such that the at least one secondary fluid chamber is reduced in size and secondary fluid is expelled from the at least one secondary fluid chamber through the fluid flow path and towards the distal end opening.

14A. The syringe of any one of examples 7A to 13A, wherein the force applied to the stopper to move the stopper within the container is less than a force applied to the plunger to move the plunger from the first engagement position to the second engagement position.

15A. The syringe of example 14A, wherein the stopper comprises at least one deformable member configured to resist movement of the plunger from the first engagement position to the second engagement position.

16A. The syringe of example 14A or example 15A, wherein the plunger is configured to snap fit into the second engagement position.

17A. The syringe of example 16A, wherein the stopper comprises at least one protrusion configured to snap-fittingly engage the plunger.

18A. The syringe of example 17A, wherein the at least one protrusion is a radially inwardly extending shoulder.

19A. The syringe of example 7A, wherein the plunger is configured to move from the first engagement position to the second engagement position after the stopper reaches a distal stop position within the container.

20A. The syringe of example 19A, wherein the stopper reaches the distal stop position when the stopper abuts an inner distal end surface of the container.

21A. The syringe of example 19A or example 20A, wherein the container comprises at least one side wall extending in an axial direction of the container and a distal end section including at least one distal end wall extending radially inwards from the at least one side wall.

22A. The syringe of example 21A, wherein the inner distal end surface is a proximally facing surface of the at least one end wall.

23A. The syringe of example 21A or example 22A, wherein the distal end section comprises a syringe tip, the syringe tip defining a syringe tip chamber that is positioned distally of the stopper when the stopper is in the distal stop position.

24A. The syringe of example 23A wherein the at least one end wall has an outer edge connected to the at least one side wall and an inner edge connected to the syringe tip, the syringe tip projecting distally from the at least one side wall.

25A. The syringe of example 24A, wherein, secondary fluid is expelled from the at least one secondary fluid chamber into the syringe tip chamber.

26A. The syringe of any one of examples 23A to 25A, wherein the distal end opening of the container is at a distal end of the syringe tip.

27A. The syringe of any one of examples 23A to 26A, wherein the syringe tip is adapted for mounting of a needle hub thereon.

28A. The syringe of examples 27A, wherein the syringe tip comprises a Luer connection element.

29A. The syringe of any one of the preceding examples, wherein the secondary fluid is a gas.

30A. The syringe of any one of examples 1A to 28A, wherein the secondary fluid is a liquid.

31A. The syringe of any one of the preceding examples, wherein a volume of the secondary fluid expelled from the at least one secondary fluid chamber is at least substantially equal to the residual volume of primary fluid.

32A. The syringe of example 31A, wherein the expelled volume of secondary fluid is greater than the residual volume of primary fluid.

33A. The syringe of example 1A, further comprising a penetrating member within the container at or adjacent to the distal end, wherein the penetrating member is configured to penetrate the stopper to create a fluid flow path for secondary fluid to exit the at least one secondary fluid chamber.

34A. The syringe of example 33A, wherein the container comprises at least one side wall extending in an axial direction of the container and a distal end section including at least one end wall extending radially inwards from the at least one side wall, wherein the penetrating member extends into the container from the at least one end wall.

35A. The syringe of example 34A, wherein the penetrating member comprises at least one side wall defining an internal lumen and at least one opening in the side wall, the lumen and opening defining the fluid flow path.

36A. The syringe of example 2A, wherein the at least one secondary fluid chamber is comprised in the plunger.

37A. The syringe of example 36A, wherein the plunger comprises a primary shaft having at least one wall defining the at least one secondary fluid chamber.

38A. The syringe of example 36A or example 37A, wherein the at least one secondary fluid chamber is comprised in an interior lumen of the primary shaft.

39A. The syringe of example 38A, wherein the plunger comprises a secondary shaft axially slidably receivable in the interior lumen of the primary shaft and wherein the secondary plunger shaft is movable towards a distal end of the primary plunger shaft to expel secondary fluid from the at least one secondary fluid chamber.

40A. The syringe of example 38A, wherein the plunger comprises a seal within the lumen, wherein the seal and the lumen together define the at least one secondary fluid chamber.

41A. The syringe of example 40A, wherein the plunger comprises a fitting at or adjacent to its proximal end, the fitting adapted to fluidly couple a secondary syringe to the lumen.

42A. The syringe of example 41A, wherein the seal is configured to be penetrated by the secondary syringe such that the secondary syringe is in fluid communication with the at least one secondary fluid chamber.

43A. The syringe of example 9A, wherein the portion of the plunger that enters into and/or moves within the stopper comprises a flange forming a fluid-tight seal with an inner surface of the secondary fluid chamber, wherein the flange moves in a distal direction within the secondary fluid chamber as the plunger moves from the first engagement position to the second engagement position.

44A. The syringe of example 43A, wherein the fluid-tight seal is maintained as the flange moves within the secondary fluid chamber.

45A. The syringe of any one of examples 2A to 32A, or 36A to 44A, wherein the plunger comprises a distal nib extending into the fluid flow path.

46A. The syringe of example 45A, wherein the syringe container comprises a distal end section comprising a syringe tip, the syringe tip defining a syringe tip chamber that is positioned distally of the stopper when the stopper is in the distal stop position, wherein the nib extends at least partially into the syringe tip chamber.

47A. The syringe of example 45A or example 46A, wherein the plunger is configured such that, when the plunger is in the second engagement position and the stopper is in the distal stop position, a distal end of the nib is positioned at or adjacent to the distal end opening of the syringe.

48A. The syringe of any one of examples 45A to 47A, wherein the plunger is configured to expel the secondary fluid around an outer surface of the nib.

49A. The syringe of any one of examples 45A to 48A, wherein the nib comprises one or more channels defined in the outer surface of the nib, the one or more channels configured to guide flow of the secondary fluid.

50A. The syringe of example 49A, wherein the one or more channels define a curved or helical path.

51A. The syringe of example 49A or example 50A, wherein the nib comprises a pair of channels positioned on opposing sides of the nib.

52A. The syringe of any one of the preceding examples, further comprising a needle engagement mechanism configured to engage a retractable needle attached to the syringe container to enable retraction of the retractable needle into the syringe container.

53A. The syringe of example 52A, wherein the needle engagement mechanism is comprised in the plunger.

54A. The syringe of example 52A or example 53A, wherein the needle engagement mechanism engages the retractable needle when the plunger is in the second engagement position.

55A. The syringe of any one of examples 52A to 54A, wherein movement of the plunger from the first engagement position to the second engagement position brings the needle engagement mechanism into engagement with the retractable needle.

56A. The syringe of any one of examples 52A to 55A, wherein the needle engagement mechanism is inhibited from engaging the retractable needle when the plunger is in the first engagement position.

57A. The syringe of any one of examples 52A to 56A, wherein the needle engagement mechanism is configured to tilt at least a cannula of the retractable needle upon retraction of the retractable needle into the syringe container.

58A. A plunger system for a syringe, the plunger system comprising:
 a stopper configured to be movably arranged within a container of the syringe; and
 a plunger engageable with the stopper and configured to apply a force to the stopper to move the stopper within the container,
  wherein the container is configured for containing a primary fluid, the container comprising a proximal end and a distal end and having a distal end opening at the distal end,
  wherein the plunger system comprises at least one secondary fluid chamber configured to contain a secondary fluid;
  wherein the plunger is configured to move the stopper towards the distal end of the container, to expel primary fluid from the container through the distal end opening; and
  wherein the plunger is configured to expel secondary fluid from the at least one secondary fluid chamber towards the distal end opening, to expel at least a portion of a residual volume of primary fluid through the distal end opening.

59A. A plunger system, the plunger system comprising:
 a stopper; and
 a plunger engageable with the stopper and configured to apply a force to the stopper,
  wherein stopper comprises at least one fluid chamber configured to contain a fluid; and
  wherein the plunger is configured to expel fluid from the at least one fluid chamber.

60A. A plunger assembly for a syringe, the plunger assembly comprising:
 a stopper configured to be movably arranged within a container of the syringe; and
 a plunger engaged with the stopper and configured to apply a force to the stopper to move the stopper within the container,
  wherein the container is configured for containing a primary fluid, the container comprising a proximal end and a distal end and having a distal end opening at the distal end,
  wherein the plunger assembly comprises at least one secondary fluid chamber configured to contain a secondary fluid;
  wherein the plunger is configured to move the stopper towards the distal end of the container, to expel primary fluid from the container through the distal end opening; and
  wherein the plunger is configured to expel secondary fluid from the at least one secondary fluid chamber towards the distal end opening, to expel at least a portion of a residual volume of primary fluid through the distal end opening.

61A. A plunger assembly, the plunger assembly comprising:
 a stopper; and
 a plunger engaged with the stopper and configured to apply a force to the stopper,
  wherein stopper comprises at least one fluid chamber configured to contain a fluid; and
  wherein the plunger is configured to expel fluid from the at least one fluid chamber.

62A. The plunger system of example 58A or example 59A, or the plunger assembly of example 60A or 61A, wherein the plunger is the plunger of any one of examples 1A-57A.

63A. The plunger system of any one of examples 58A, 59A or 62A, or the plunger assembly of any one of examples 60A, 61A or 62A, wherein the stopper is the stopper of any one of examples 1A-57A.

64A. A stopper comprising at least one fluid chamber configured to contain a fluid, wherein the stopper is configured to be engaged by a plunger to apply a force to the stopper and to expel fluid from the at least one fluid chamber.

65A. A plunger configured for engagement with a stopper, the stopper having at least one fluid chamber configured to contain a fluid, wherein the plunger is configured to apply a force to the stopper and to expel fluid from the at least one fluid chamber.

66A. A method of expelling fluid from a syringe according to any one of the preceding examples, the method comprising:
 engaging the plunger with the stopper;
 applying force to the plunger to at least partially transmit the force to the stopper to move the stopper within the container towards the distal end of the container, expelling primary fluid from the container through the distal end opening; and applying further force to the plunger to expel secondary fluid from the at least one secondary fluid chamber towards the distal end opening, expelling at least a portion of a residual volume of primary fluid through the distal end opening.

67A. The method of example 66A, wherein the first force is applied to the plunger to move the stopper within the container towards the distal end of the container, expelling primary fluid from the container through the distal end opening and a second force is applied to the plunger to expel secondary fluid from the at least one secondary fluid chamber towards the distal end opening.

68A. The method of example 67A, wherein the second force is greater than the first force.

69A. The method of example 67A or example 68A wherein application of the second force moves the plunger from a first engagement position with the stopper to a second engagement position with the stopper and wherein, when the plunger moves from the first engagement position to the second engagement position, secondary fluid is expelled from the at least one secondary fluid chamber through the fluid flow path and towards the distal end opening.

70A. The method of any one of examples 67A to 69A, wherein application of the second force causes at least a portion of the plunger to enter into a chamber in the stopper.

71A. The method of any one of examples 67A to 70A, wherein application of the second force overcomes resistance of at least one deformable member configured to resist movement of the plunger from the first engagement position to the second engagement position.

72A. The method of any one of examples 67A to 71A, wherein the second force is applied after the stopper reaches a distal stop position within the container.

73A. The method of any one of examples 67A to 72A, wherein the primary fluid is expelled through a cannula of an attached retractable needle, wherein the method further comprises comprising engaging the plunger with the retractable needle by a needle engagement mechanism and applying withdrawing force to the plunger to withdraw the retractable needle into the syringe container.

74A. The method of example 73A, wherein movement of the plunger from the first engagement position to the second engagement position causes the needle engagement mechanism to engage the retractable needle.

75A. The method of any one of examples 63A to 74A, further comprising snapping the plunger shaft after use to inhibit re-use of the syringe.

76A. The syringe of example 1B, further comprising any of the examples 2A to 57A.

77A. The syringe of example 1C, further comprising any of the examples 2A to 57A.

1D. A syringe comprising:
    a container for containing a primary fluid;
    means for expelling primary fluid from the container; and
    means for expelling at least a portion of a residual volume of primary fluid from the container.

2D. A syringe comprising:
    a container for containing a primary fluid, the container comprising a proximal end and a distal end and having a distal end opening at the distal end;
    means for expelling primary fluid from the container through the distal end opening; and
    means for expelling at least a portion of a residual volume of primary fluid through the distal end opening.

3D. A syringe comprising:
    a container for containing a primary fluid, the container comprising a proximal end and a distal end and having a distal end opening at the distal end, the container further comprising at least one secondary fluid chamber configured to contain a secondary fluid;
    means for expelling primary fluid from the container through the distal end opening; and
    means for expelling secondary fluid from the at least one secondary fluid chamber, thereby to expel at least a portion of a residual volume of primary fluid through the distal end opening.

4D. The syringe of example 1D, further comprising any of the examples 2A to 57A.

5D. The syringe of example 2D, further comprising any of the examples 2A to 57A.

6D. The syringe of example 3D, further comprising any of the examples 2A to 57A.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A syringe comprising:
    a container for containing a primary fluid, the container comprising a proximal end and a distal end and having a distal end opening at the distal end;
    a stopper movably arranged within the container, and
    a plunger engageable with the stopper and configured to apply a force to the stopper to move the stopper within the container;
    wherein the stopper comprises at least one secondary fluid chamber configured to contain a secondary fluid and at least one fluid flow path for secondary fluid to exit the at least one secondary fluid chamber;
    wherein the plunger is movably engageable with the stopper between a first engagement position and a second engagement position,
    wherein, when the plunger is in the first engagement position the secondary fluid in the at least one secondary fluid chamber is contained entirely therein, and the plunger is configured to move the stopper towards the distal end of the container, to expel the primary fluid from the container through the distal end opening;
    wherein, when the plunger moves from the first engagement position to the second engagement position, at least a portion of the plunger moves through the at least one secondary fluid chamber in the stopper to expel secondary fluid from the at least one secondary fluid chamber through the fluid flow path towards the distal end opening, to expel at least a portion of a residual volume of primary fluid through the distal end opening,
    wherein the at least one fluid flow path comprises a channel extending through material of the stopper, and
    wherein the plunger comprises a nib at a distal end of the plunger, the nib extending into the channel of the fluid flow path when the plunger is in the first engagement position and when the plunger is in the second engagement position.

2. The syringe of claim 1, wherein, as the plunger moves from the first engagement position to the second engagement position, the at least a portion of the plunger that moves through the at least one secondary fluid chamber displaces secondary fluid in the at least one secondary fluid chamber so that the displaced secondary fluid is expelled through the fluid flow path and towards the distal end opening.

3. The syringe of claim 1, wherein the plunger is configured to move from the first engagement position to the second engagement position after the stopper reaches a distal stop position within the container.

4. The syringe of claim 1, wherein the portion of the plunger that moves through the stopper comprises a flange forming a fluid-tight seal with an inner surface of the secondary fluid chamber, wherein the flange moves in a distal direction within the secondary fluid chamber as the plunger moves from the first engagement position to the second engagement position.

5. The syringe of claim 4, wherein the fluid-tight seal is maintained as the flange moves within the secondary fluid chamber.

6. The syringe of claim 1, wherein the container comprises a distal end section comprising a syringe tip, the syringe tip defining a syringe tip chamber that is positioned distally of the stopper when the stopper is in a distal stop position, wherein the nib extends at least partially into the syringe tip chamber.

7. The syringe of claim 1, wherein the plunger is configured such that, when the plunger is in the second engagement position and the stopper is in the distal stop position, a distal end of the nib is positioned at or adjacent to the distal end opening of the syringe.

8. The syringe of claim 1, wherein the nib comprises one or more channels defined in an outer surface of the nib, the one or more channels configured to guide flow of the secondary fluid around an outer surface of the nib.

9. The syringe of claim 8, wherein the one or more channels define a curved or helical path.

10. The syringe of claim 1, further comprising a needle engagement mechanism configured to engage a retractable needle attached to the container to enable retraction of the retractable needle into the container,
wherein the needle engagement mechanism is comprised in the plunger,
wherein movement of the plunger from the first engagement position to the second engagement position brings the needle engagement mechanism into engagement with the retractable needle.

11. The syringe of any claim 10, wherein the needle engagement mechanism is inhibited from engaging the retractable needle when the plunger is in the first engagement position.

12. The syringe of claim 10, wherein the needle engagement mechanism is configured to tilt at least a cannula of the retractable needle upon retraction of the retractable needle into the container.

13. The syringe of claim 1, wherein the force applied to the stopper to move the stopper within the container is less than a force applied to the plunger to move the plunger from the first engagement position to the second engagement position.

14. The syringe of claim 1, wherein the stopper comprises at least one resiliently deformable member configured to resist movement of the plunger from the first engagement position to the second engagement position.

15. The syringe of claim 14, wherein the at least one resiliently deformable member comprises a radially inwardly extending shoulder.

16. The syringe of claim 1, wherein the at least one secondary fluid chamber is sealed when the plunger is in the first engagement position.

17. The syringe of claim 16, wherein the stopper further comprises a sealing flange forming a fluid-tight seal around the plunger.

18. A plunger system for a syringe, the plunger system comprising:
a stopper configured to be movably arranged within a container of the syringe; and
a plunger engageable with the stopper and configured to apply a force to the stopper to move the stopper within the container,
wherein the container is configured for containing a primary fluid, the container comprising a proximal end and a distal end and having a distal end opening at the distal end,
wherein the stopper comprises at least one secondary fluid chamber configured to contain a secondary fluid and at least one fluid flow path for secondary fluid to exit the at least one secondary fluid chamber,
wherein the plunger is movably engageable with the stopper between a first engagement position and a second engagement position,
wherein, when the plunger is in the first engagement position the secondary fluid in the at least one secondary fluid chamber is contained entirely therein, and the plunger is configured to move the stopper towards the distal end of the container, to expel the primary fluid from the container through the distal end opening,
wherein, when the plunger moves from the first engagement position to the second engagement position, the plunger is configured to expel secondary fluid from the at least one secondary fluid chamber through the fluid flow path towards the distal end opening, to expel at least a portion of a residual volume of primary fluid through the distal end opening,
wherein the at least one fluid flow path comprises a channel extending through material of the stopper, and
wherein the plunger comprises a nib at a distal end of the plunger, the nib extending into the channel of the fluid flow path when the plunger is in the first engagement position and when the plunger is in the second engagement position.

19. The plunger system of claim 17, wherein the sealing flange forms a fluid-tight seal around the nib.

20. A method of expelling fluid from a syringe according claim 1, the method comprising:
engaging the plunger with the stopper;
applying a first force to the plunger to at least partially transmit the first force to the stopper to move the stopper within the container towards the distal end of the container, expelling primary fluid from the container through the distal end opening; and
applying a second force to the plunger to expel secondary fluid from the at least one secondary fluid chamber towards the distal end opening, expelling a residual volume of primary fluid through the distal end opening.

21. The method of claim 20, wherein the second force is greater than the first force.

* * * * *